US011596547B2

(12) United States Patent
Keller et al.

(10) Patent No.: US 11,596,547 B2
(45) Date of Patent: Mar. 7, 2023

(54) HYDRODISSECTION AND POSTERIOR CAPSULE OPACIFICATION PREVENTION DURING CAPSULOTOMY PROCEDURE

(71) Applicant: Centricity Vision, Inc., Fremont, CA (US)

(72) Inventors: Christopher Guild Keller, El Cerrito, CA (US); Thomas Haynes McGaffigan, Saratoga, CA (US); Kevin L. Waltz, Indianapolis, IN (US); Thomas Milton McNicholas, Laguna Niguel, CA (US)

(73) Assignee: CENTRICITY VISION, INC., Carlsbad, CA (US)

( * ) Notice: Subject to any disclaimer, the term of this patent is extended or adjusted under 35 U.S.C. 154(b) by 1078 days.

(21) Appl. No.: 16/257,477

(22) Filed: Jan. 25, 2019

(65) Prior Publication Data
US 2019/0231593 A1    Aug. 1, 2019

Related U.S. Application Data

(60) Provisional application No. 62/624,696, filed on Jan. 31, 2018, provisional application No. 62/721,182, filed on Aug. 22, 2018.

(51) Int. Cl.
*A61F 9/007* (2006.01)
*A61F 9/008* (2006.01)
(Continued)

(52) U.S. Cl.
CPC .......... *A61F 9/00754* (2013.01); *A61B 18/08* (2013.01); *A61F 2/16* (2013.01);
(Continued)

(58) Field of Classification Search
CPC ........ A61F 9/00754; A61F 2/16; A61F 9/008; A61F 2009/00889; A61B 18/08;
(Continued)

(56) References Cited

U.S. PATENT DOCUMENTS 4,736,836 A    4/1988  Alongi et al.
5,066,297 A *  11/1991  Cumming .............. A61B 17/29
                                                    606/107
(Continued)

FOREIGN PATENT DOCUMENTS

WO    WO 2014/047478 A1    3/2014

OTHER PUBLICATIONS

Auffarth, G. et al., "Comparison of Nd: YAG capsulotomy rates following phacoemulsification with implantation of PMMA, silicone, or acrylic intra-ocular lenses in four European countries," Ophthalmic Epidemiology, Jul. 8, 2004, vol. 2, pp. 319-329.
(Continued)

*Primary Examiner* — Gary Jackson
*Assistant Examiner* — Sebastian X Lukjan
(74) *Attorney, Agent, or Firm* — Fenwick & West LLP

(57) ABSTRACT

Embodiments of the invention provide hydrodissection and/or PCO prevention or reduction in a patient undergoing eye surgery. In one embodiment, the invention is a surgical device for cutting and excising a portion of tissue, for example in performing a lens capsulotomy. A capsulotomy tip is inserted into an eye through an incision in the surface of the eye. The capsulotomy tip includes a suction cup to provide suction to the lens capsule. Then suction is applied via the suction cup to secure the capsulotomy tip to the eye. In some embodiments, after the capsulotomy tip is secured to the lens capsule, a cutting element of the capsulotomy tip is used to cut a tissue of the eye. Fluid is pushed through the capsulotomy tip and the capsulotomy tip is removed from
(Continued)

the eye. Moreover, disclosed is an intraocular lens (IOL) to be used in conjunction with the surgical device.

22 Claims, 25 Drawing Sheets

(51) Int. Cl.
| | |
|---|---|
| *A61B 18/08* | (2006.01) |
| *A61F 2/16* | (2006.01) |
| *A61M 1/00* | (2006.01) |
| *A61B 18/00* | (2006.01) |

(52) U.S. Cl.
CPC ............. *A61F 9/008* (2013.01); *A61M 1/77* (2021.05); *A61B 2018/00291* (2013.01); *A61B 2018/00321* (2013.01); *A61B 2018/00601* (2013.01); *A61F 2009/00889* (2013.01)

(58) Field of Classification Search
CPC .......... A61B 2018/00291; A61B 2018/00321; A61B 2018/00601; A61M 1/0058; A61M 1/77
See application file for complete search history.

(56) References Cited

U.S. PATENT DOCUMENTS

| | | | |
|---|---|---|---|
| 6,186,148 B1 | 2/2001 | Okada | |
| 6,217,543 B1* | 4/2001 | Anis | A61F 9/00763 604/22 |
| 8,157,797 B2* | 4/2012 | Boukhny | A61F 9/00754 606/45 |
| 8,702,698 B2 | 4/2014 | Keller | |
| 10,206,816 B2 | 2/2019 | Keller | |
| 2002/0072795 A1 | 6/2002 | Green | |
| 2004/0260254 A1* | 12/2004 | Neilson | A61F 9/0017 604/297 |
| 2008/0221500 A1 | 9/2008 | Sniegowski et al. | |
| 2009/0088734 A1 | 4/2009 | Mordaunt | |
| 2010/0286651 A1* | 11/2010 | Sorensen | A61M 1/0058 604/151 |
| 2010/0312232 A1* | 12/2010 | Jia | A61B 18/10 606/29 |
| 2013/0197548 A1 | 8/2013 | Keller | |
| 2014/0207137 A1 | 7/2014 | Keller | |
| 2016/0143778 A1* | 5/2016 | Aljuri | A61B 8/10 606/107 |
| 2017/0347877 A1* | 12/2017 | Frey | A61F 9/00834 |

OTHER PUBLICATIONS

Buehl, W. et al., "Long-term effect of optic edge design in an acrylic intraocular lens on posterior capsule opacification," J Cataract Refract Surg, 2005, vol. 31, pp. 954-961.
Findl, O. et al., "Long-term Effect of Sharp Optic Edges of a Polymethyl Methacrylate Intraocular Lens on Posterior Capsule Opacification," Ophthalmology, 2005, vol. 112, pp. 2004-2008.
Kohnen, T. et al., "Optic Edge Design as Long-term Factor for Posterior Capsular Opacification Rates," Ophthalmology, Aug. 2008, vol. 115, No. 8, pp. 1308-1314.
Nishi, O. et al., "Effect of intraocular lenses on preventing posterior capsule opacification: Design versus material," Journal of Cataract & Refractive Surgery, Oct. 2004, vol. 30, No. 10, pp. 2170-2176.
Nishi, O. et al., "Inhibition of migrating lens epithelial cells at the capsular bend created by the rectangular optic edge of a posterior chamber intraocular lens," Ophthalmic Surg Lasers, Jul. 1998, vol. 29, No. 7, pp. 587-594 (abstract only).
Nishi, O. et al., "Preventing lens epithelial cell migration using intraocular lenses with sharp rectangular edges," J Cataract Refract Surg, Oct. 2000, vol. 26, pp. 1543-1549.
Schaumberg, D.A. et al., "A Systematic Overview of the Incidence of Posterior Capsule Opacification," Ophthalmology, 1998, vol. 105, No. 7, pp. 1213-1221.
Tetz, M. et al., "New Hydrophobic IOL Material and Understanding the Science of Glistenings," Current Eye Research, 2015, vol. 40, No. 10, pp. 969-981.
Waltz, K.L. et al., "Precision Pulse Capsulotomy: Initial Clinical Experience in Simple and Challenging Cataract Surgery," JCRS, 2017, vol. 43, pp. 606-614.
Wormstone, M., "Posterior Capsule Opacification: A Cell Biological Perspective," Exp. Eye Res., 2002, vol. 74, pp. 337-347.
PCT International Search Report and Written Opinion, PCT Application No. PCT/US2019/015311, dated Apr. 23, 2019, 20 pages.

* cited by examiner

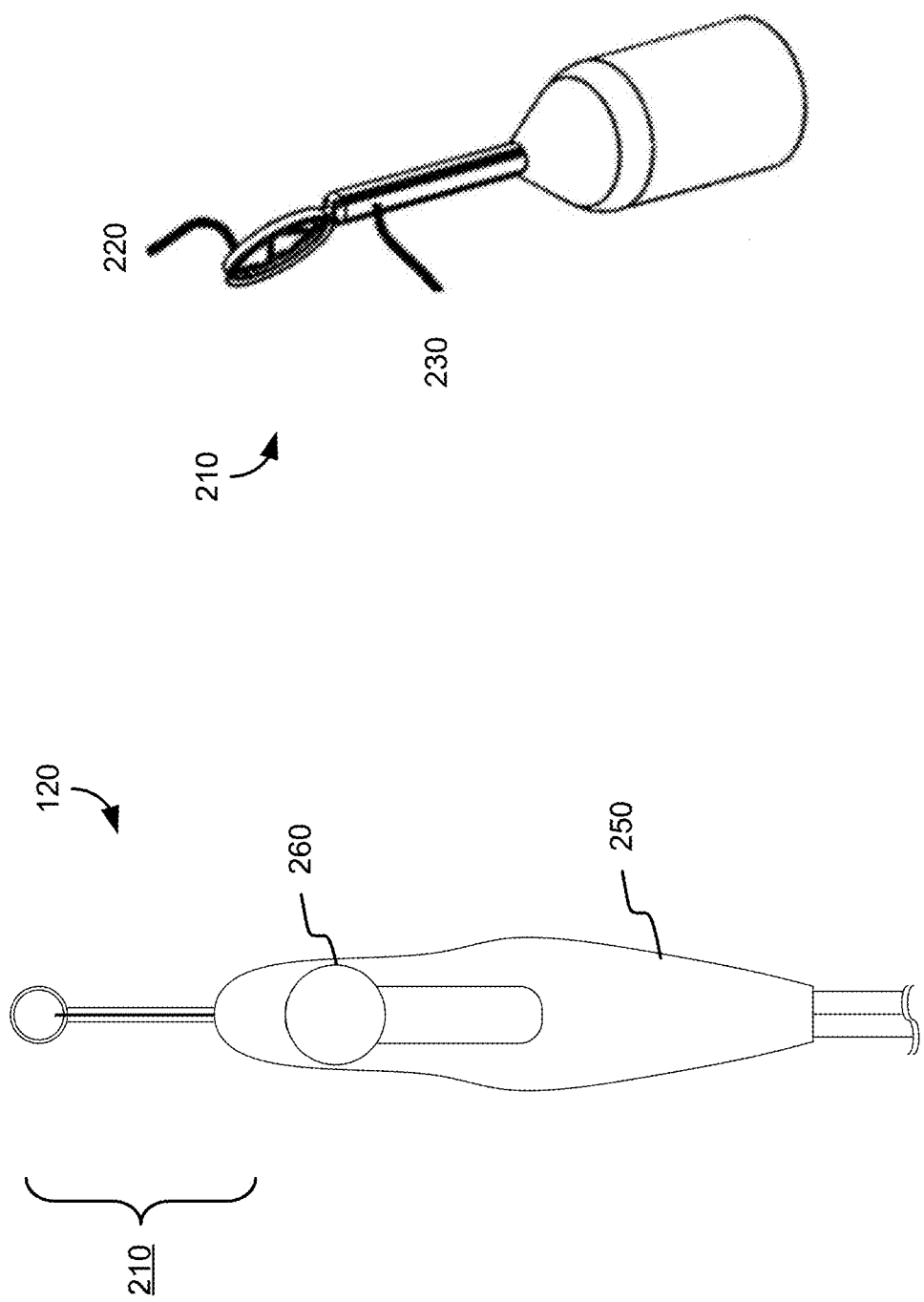

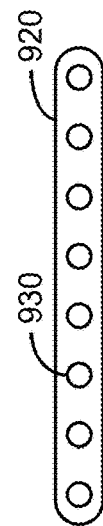
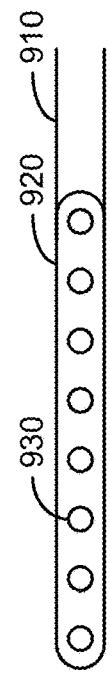
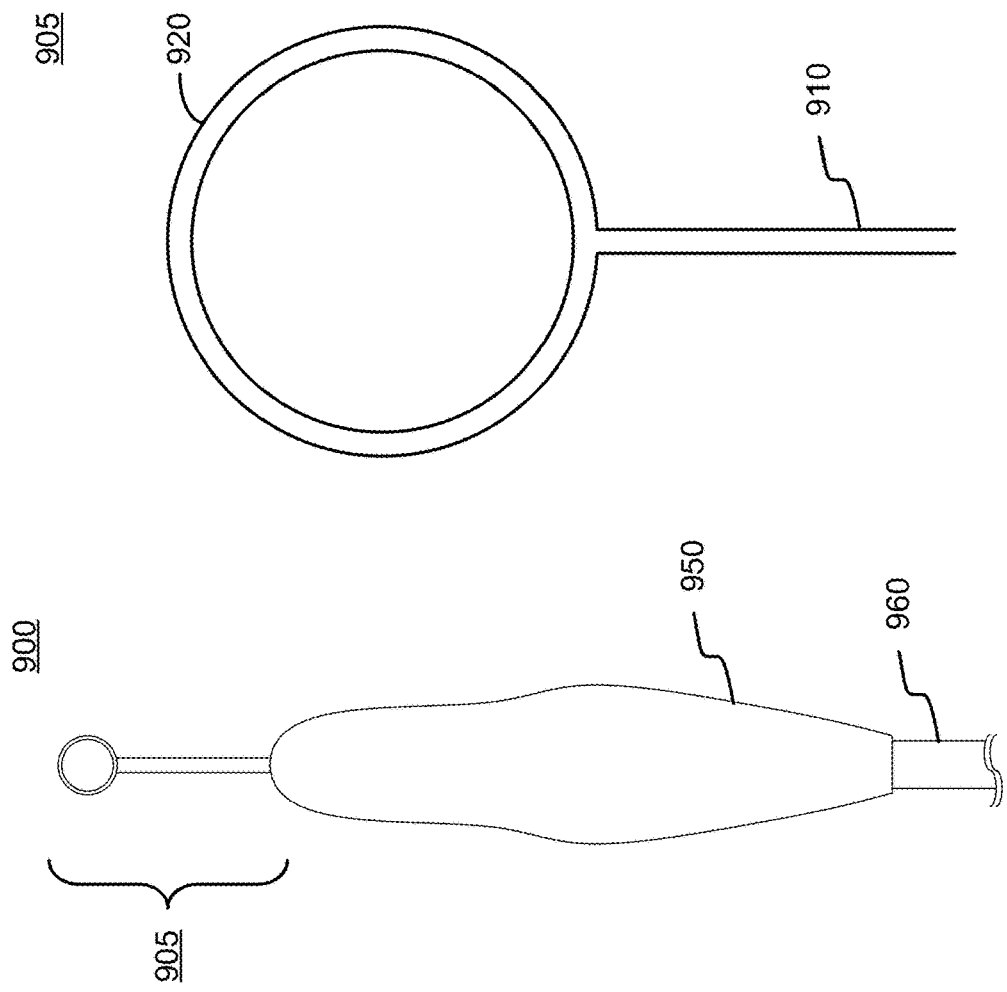

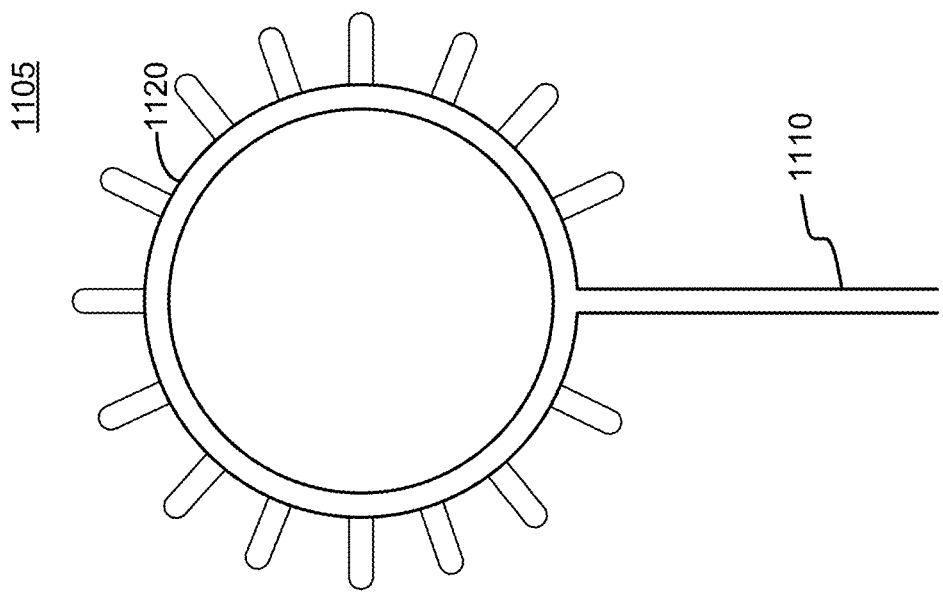
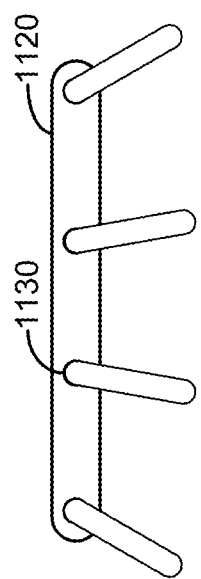
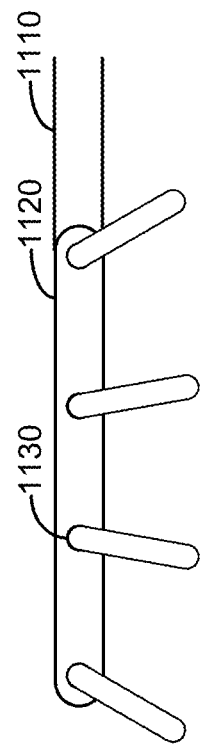

| | Intervention | Months After Surgery | N | % PCO coverage | Statistical Analysis (GEE Model) |
|---|---|---|---|---|---|
| Unadjusted | Zepto | 13-21 | 37 | 20 | p <0.0001 |
| | CCC | 13-21 | 23 | 77 | |
| Adjusted | Zepto | 13-21 | 32 | 8 | p <0.0001 |
| | CCC | 13-21 | 21 | 83 | |

HYDRODISSECTION AND POSTERIOR CAPSULE OPACIFICATION PREVENTION DURING CAPSULOTOMY PROCEDURE

CROSS-REFERENCE TO RELATED APPLICATIONS

This application claims the benefit of U.S. Provisional Patent Application No. 62/624,696, filed Jan. 31, 2018 and U.S. Provisional Patent Application No. 62/721,182, filed Aug. 22, 2018, the contents of which are incorporated herein by reference.

GOVERNMENT SUPPORT

This invention was made with government support under grant no. R44EY021023, awarded by the National Institutes of Health. The government has certain rights in the invention.

BACKGROUND

1. Field of the Disclosure

This invention relates generally to microsurgery of the eye, and more specifically to lens cataract surgery.

2. Description of the Related Art

Posterior capsule opacification (PCO) develops over the clear posterior capsule a few months, to a few years after an uneventful cataract surgery. PCO results from the growth and abnormal proliferation of lens epithelial cells (LECs) that may still remain on the capsule after the removal process at the time of cataract surgery. The LECs migrate to the posterior capsule where they approach the central visual axis and cause visual axis obscuration, resulting in deterioration of vision. While treatments of PCO currently exist, they come at additional socioeconomic cost, and it is beneficial to reduce the occurrence of PCO altogether.

In addition, separate from PCO, a procedure of hydrodissection is commonly used in cataract and other eye surgeries for separation of the lens of the eye from the lens capsule surrounding the eye. In some cases, there are adhesions between the cataractous lens and the lens capsule surrounding it, so hydrodissection delivers liquid to the area between the lens and the lens capsule to allow removal of the lens from the eye. However, this hydrodissection is commonly manually performed and does not deliver liquid evenly around the lens. It is a separate step in the cataract removal process involving introduction of an instrument for delivery of the liquid, and thus adds some extra time and complication to the eye surgery.

As a result of PCO, surgeons perform cataract surgery using square-edged intraocular lenses (IOLs) to replace the cataractous lens of the patient, since these square-edged IOLs are reported to help to reduce the incidence of or retard development of PCO. However, square-edged IOLs are known to be a primary cause of dysphotopsia in patients following a cataract surgery, due in part to the reflection from the edge of the IOL. Dysphotopsia in a patient results in the patient seeing unwanted images, such as undesired light or flashes after surgery (positive dysphotopsia) or an undesired arc-shaped shadow (negative dysphotopsia). Thus, while square-edged IOLs have some benefit with regard to PCO, they also have a clear downfall due to the commonly resulting dysphotopsias.

SUMMARY

Embodiments of the invention provide for PCO prevention or reduction in a patient undergoing cataract surgery or other forms of eye surgery, and embodiments further provide for hydrodissection for separation of a lens in the eye from the lens capsule. In one embodiment, the invention is a surgical device for cutting and excising a portion of tissue, for example in performing a lens capsulotomy in an eye. A capsulotomy tip is inserted into an eye of a patient through an incision in the surface of the eye. The capsulotomy tip includes a suction cup that utilizes suction for creating pressure to the cutting element and subsequently to the capsule of the eye. The suction is applied via the console, tubing, and suction cup thus securing the capsulotomy tip to the eye of the patient. In some embodiments, after the capsulotomy tip is secured to the lens capsule of the eye, a cutting element included in the capsulotomy tip is used to cut tissue of the eye of the patient. Pressurized fluid via a fluid delivery mechanism, such as a hand held roller dispenser, is delivered to the capsulotomy tip and the suction cup. The pressurized fluid entering the suction cup and tip, causes the cup and tip to be easily removed from the eye of the patient.

Other aspects of the disclosure include a surgical device including a suction cup, a lumen coupled to the suction cup, and a dispenser device coupled to the tubing connected to the lumen. In some embodiments, the suction cup includes an inner diameter wall, an outer diameter wall, and a roof. The inner diameter wall, the outer diameter wall, and the roof form a cavity having a channel that distributes flow throughout the cavity. The lumen of the stem is coupled to the tubing that in turn is connected to the vacuum source. The suction cup may further include a lip that is coupled to the outer diameter wall, and is configured to be pulled against a capsular membrane of the eye to form a seal to allow a suction pressure inside the suction cup chamber to decrease. In some embodiments, the roller dispenser is configured to dispense a predetermined amount of fluid when the roller of the roller dispenser is advanced along a linear track. Each of the surgical procedures and devices described herein, can reduce or prevent PCO via one or more aspects of the device. The PCO reduction or prevention can occur by delivery of suction to a suction cup, delivery of pressurized fluid into the suction cup which also releases the suction cup from the lens capsule, and applying pressure to the cutting element of the lens capsule tissue. In another of the surgical procedures and devices described herein, the delivery of pressurized fluid into the suction cup to release the suction cup from the capsule causes a circumferential fluid wave to travel in the plane separating the lens cortex from the undersurface of the capsule. This fluid wave causes hydrodissection of the lens freeing the lens within the capsular bag. Additionally, the circumferential fluid wave affects LEC attachment and/or viability and thus lessen the occurrence of PCO. These and other mechanisms may kill or damage the epithelial cells inside the eye or otherwise prevent/reduce the LECs that form on the capsule or that may provide some other anti-PCO property during surgery. These are described in more detail below.

Still further aspects of the disclosure include a device and procedure for hydrodissection via delivery of liquid with a hydrodissection device. In one embodiment, the hydrodissection is provided via one or more of the surgical devices described above for performing a capsulotomy. This thus simplifies the hydrodissection procedure in that it is not a separate step in the cataract removal process involving introduction of a separate instrument for delivery of the liquid, but instead the capsulotomy device also performs this hydrodissection during or following performance of the capsulotomy. This design thus saves time and complication in the cataract removal process. In addition, because of the design of the device including the suction cup that forms a seal with the lens capsule and the delivery of pressurized fluid with this instrument, the fluid is delivered generally evenly around the lens, as opposed to the conventional delivery mechanism that typically delivers fluid less evenly. In another embodiment, the hydrodissection device is a separate instrument from the capsulotomy instrument, but is still designed for even delivery of fluid around the lens based on its structure.

In addition, the surgical device can minimize the incidence of dysphotopsia. A square-edged IOL is not required when the surgical device is used because the surgical device itself reduces or removes the PCO effect. The surgical device can thus be used with a less-square or non-square edged IOLs that are less likely to result in reflections that commonly cause dysphotopsia in the patient after the cataract surgery. Thus, in one embodiment, the invention includes a less-square or non-square edged IOL, or an IOL that is designed specifically for use with the surgical device. The surgical device can be packaged with this specially designed IOL.

BRIEF DESCRIPTION OF THE DRAWINGS

FIG. 2A illustrates a capsulotomy device, according to one embodiment.

FIG. 2B illustrates components of a capsulotomy tip, according to one embodiment.

FIG. 9A illustrates a hydrodissection/anti-PCO device, according to one embodiment.

FIG. 9B is a top view of the hydrodissection/anti-PCO tip, according to one embodiment.

FIG. 9C is a front view of the hydrodissection/anti-PCO tip, according to one embodiment.

FIG. 9D is a side view of the hydrodissection/anti-PCO tip, according to one embodiment.

FIG. 11A is a top view of the hydrodissection/anti-PCO tip, according to the third embodiment.

FIG. 11B is a front view of the hydrodissection/anti-PCO tip, according to the third embodiment.

FIG. 11C is a side view of the hydrodissection/anti-PCO tip, according to the third embodiment.

FIG. 20 illustrates the percentage of cataract patients who develop PCO when capsulotomies are performed using various capsulotomy techniques.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Embodiments of the invention provide for PCO prevention or reduction following a cataract surgery or other eye surgery. The embodiments are generally described in the context of a lens capsule surgery in which a portion of the anterior or posterior surface of a lens capsule is cut to create an opening in the lens capsule. The technique may be used for performing a treatment for cataracts in which the lens located within the capsule is removed from the eye through the opening created in the lens capsule. Moreover, the techniques and devices described herein may be useful tools for performing other medical procedures (such as corneal surgeries, or posterior capsulotomies, or surgeries involving tissue other than tissue of the eye). The methods and devices described throughout will be described in the context of lens capsulotomy for illustration, and the methods and devices will be referred to as capsulotomies and capsulotomy devices, respectively. However, it is to be understood that the methods and devices are not limited to capsulotomy procedures, and can be used for other medical procedures. In addition, in some embodiments, hydrodissection and/or PCO prevention or reduction is provided via a standalone device used alongside other surgical instruments (e.g., cataract surgery instruments, capsulotomy instruments, etc.). Various embodiments of instruments and methods are described first below, followed by a description of PCO prevention that can occur with the aforementioned devices and methods.

Capsulotomy System

Figure 1A:
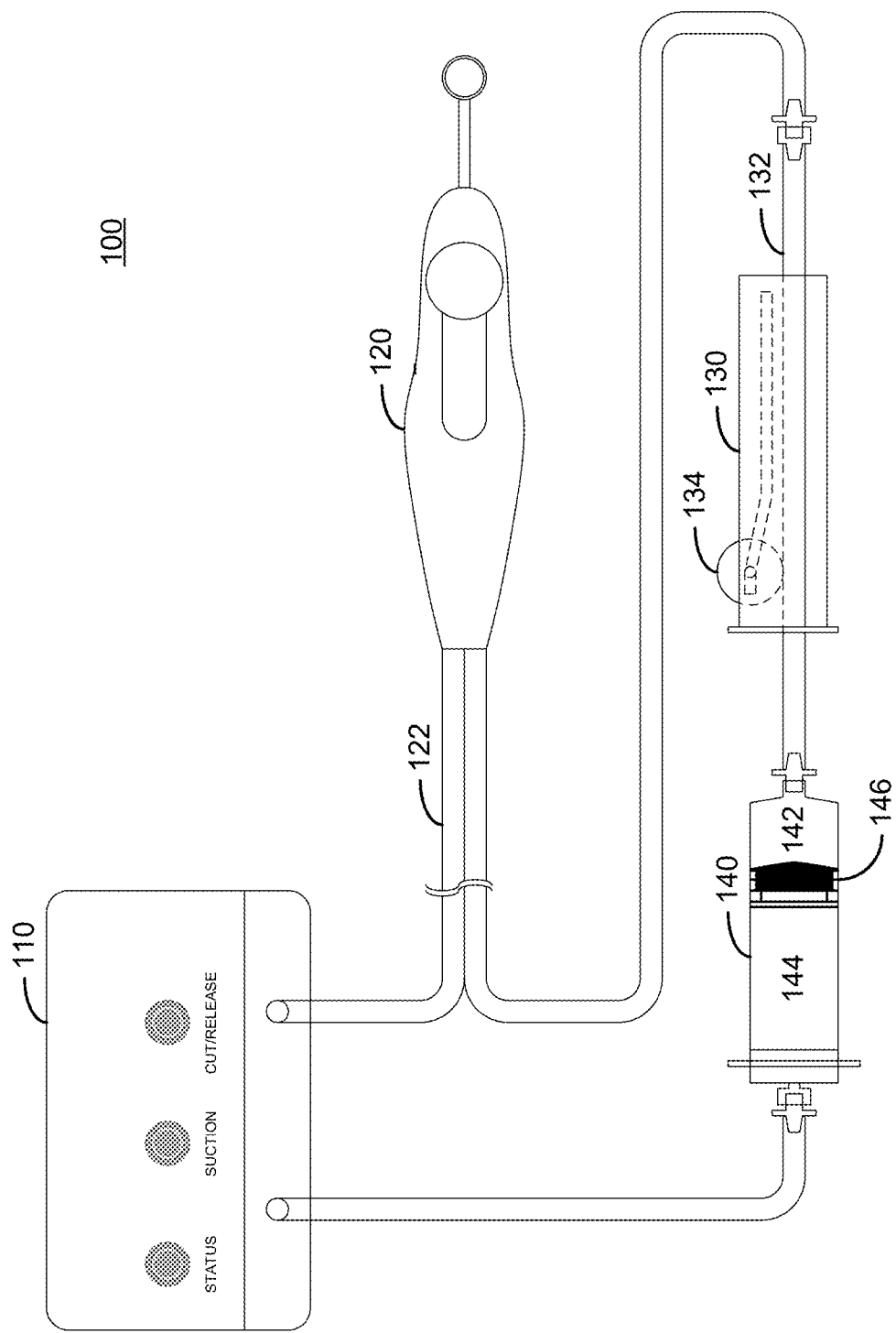
FIG. 1A illustrates a capsulotomy system, according to one embodiment.

FIG. 1A illustrates a capsulotomy system 100, according to one embodiment. The capsulotomy system 100 includes a console 110, a capsulotomy device 120, a roller dispenser 130, and a fluid isolator 140.

The console 110 provides power and suction to the capsulotomy device 120. In some embodiments, the console 110 includes a processor that is programmed to execute a predetermined program in response to inputs from a user (e.g., a nurse or a doctor). For example, the console is configured to apply a predetermined suction force in response to the user pressing the "suction" button, and to supply a predetermined current waveform in response to the user pressing the "cut/release" button.

The capsulotomy device 120 is operated by a user, such as a doctor, to excise a circular portion from a lens capsule from the eye of a patient. The capsulotomy device 120 is electrically coupled to the console 110 and receives a preset current waveform for operating a cutting element disposed on a tip of the capsulotomy device 120. In some embodiments, the capsulotomy device is electrically connected to the console via cable 122. The capsulotomy device 120 is further coupled to a suction/vacuum pump, or a peristaltic pump of the console 110. In some embodiments (e.g., when a vacuum pump is used), the capsulotomy device is coupled to the pump through the fluid isolator 140. In other embodiments (e.g., when a peristaltic pump is used) the capsulotomy device is connected to pump the console without a fluid isolator. Thus, the console 110 may apply suction to the eye of the patient through a suction cup disposed on the tip of the capsulotomy device, where a suction cup is included in the device. A detailed description of the capsulotomy device 120 is provided hereinbelow in conjunction with FIG. 2A.

The fluid isolator 140 isolates the fluid used in the capsulotomy device 120 from the suction provided by the console 110. The fluid isolator includes a fluid end 142 and a vacuum/atmospheric vent end 144. The fluid end 142 and the vacuum end 144 are separated by a floating piston 146. The console 110 provides suction to vacuum end 144 of the fluid isolator 140 and the vacuum acts on the floating piston 146 creating suction on the opposite side of the floating piston. As the piston 146 of the fluid isolator 140 is moved, fluid from the tube connected to the fluid end 142 of the fluid isolator 140 is drawn into the fluid end 142, thus applying vacuum through the tube to a suction cup of the capsulotomy device. The fluid filled line provides for rapid generation of suction inside the suction cup. A detailed description of the fluid isolator 140 is provided hereinbelow in conjunction with FIG. 4A through FIG. 4C.

The roller dispenser 130 is configured to pinch off the fluid filled line and dispense fluid in tube 132, and to push a preset amount of fluid through the tube as a roller 134 is rolled forward. A detailed description of the roller dispenser 130 is provided hereinbelow in conjunction with FIG. 5A through FIG. 5C.

Capsulotomy Tip

FIG. 2A illustrates a capsulotomy device, and FIG. 2B illustrates components of a capsulotomy tip, according to one embodiment. The capsulotomy device 120 includes a capsulotomy tip 210, a handle 250, and a manipulation device 260. In some embodiments, the capsulotomy tip 210 is a disposable unit that can be attached and detached from a capsulotomy handpiece. In other embodiments, the capsulotomy tip is permanently attached to the capsulotomy handpiece.

The capsulotomy tip 210 with self-contained suction can include a suction cup 220, and a suction tube 230 within a handle (or elsewhere). In some embodiments, the capsulotomy tip further includes an expandable chamber in fluid communication with the suction cup, for creating suction. In some embodiments, a component other than the expandable chamber and suction tube generates and provides suction to the suction cup. In some embodiments, the suction cup 220 is collapsible to a small cross section so that it can be inserted through a corneal incision (e.g., an incision of less than 3.0 mm in length) or a scleral incision. A corneal incision is made in the cornea of the eye via a scalpel or other instrument, and the suction cup is collapsed or stretched to pass through the incision, and it returns to its original shape once inside the cornea.

The suction cup 220 can be made of an elastomeric material such as silicone or polyurethane (e.g., made by casting or by injection molding), though other materials can be used as well. The thinner the walls of the suction cup are, the stiffer (higher durometer) the material can be. The size range for the suction cup would commonly range from about 3.5 mm to about 7 mm in diameter, while the height would commonly range from about 0.5 mm to about 1.5 mm.

However, other suction cup and cutting element sizes and designs are possible for different applications such as various animals such as canines. After insertion into the anterior chamber of the eye, the device is designed to rapidly return to its circular shape. The suction cup 220 generally has a roof and an underside. Different designs of a suction cup are illustrated in U.S. Pat. No. 8,702,698, U.S. Patent Application Publication No. 2013/0197548, U.S. Patent Application Publication No. 2014/0207137, U.S. patent application Ser. No. 14/353,220, and International Patent Application No. PCT/US2013/060988, which are hereby incorporated by reference herein in their entireties. Any of these designs can be used with the devices described herein.

Figure 2C:
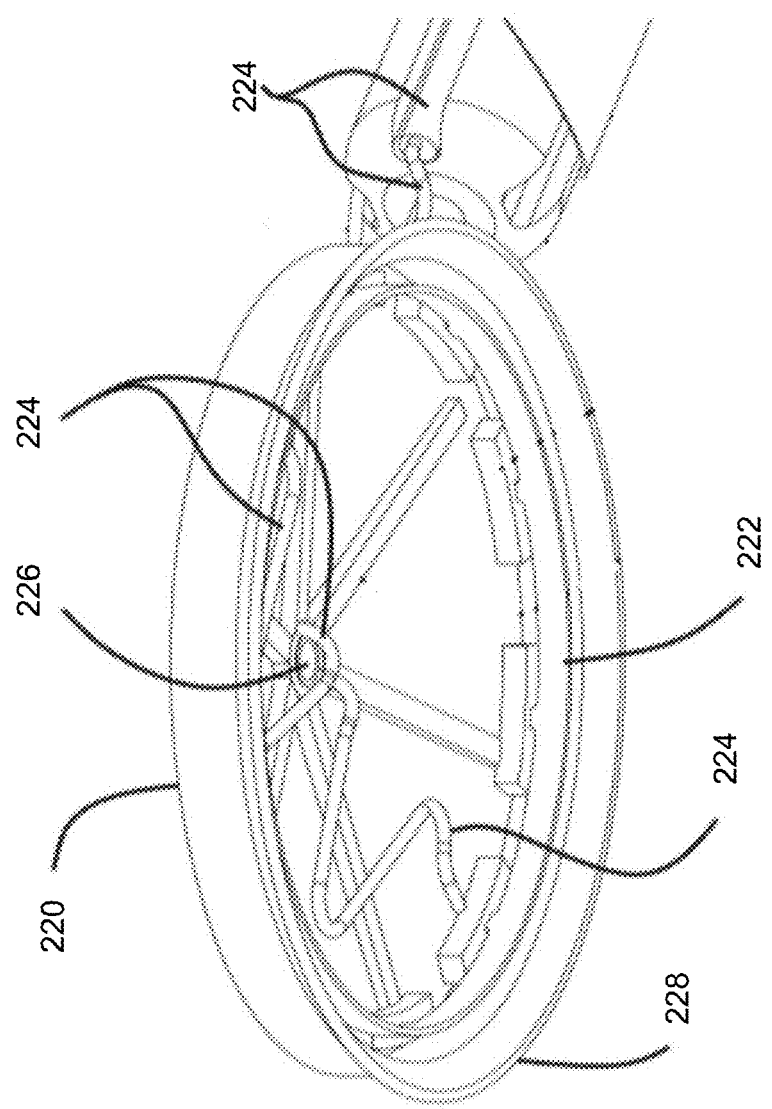
FIG. 2C illustrates an underside of a suction cup roof of a capsulotomy device, according to one embodiment.

FIG. 2C illustrates an underside of a suction cup roof of a capsulotomy device, according to one embodiment. Specifically, FIG. 2C shows the underside of the capsulotomy device, depicting a relationship between a cutting element 222 and the suction cup 220. In this embodiment, the cutting element 222 is attached to the underside of the suction cup roof, for example via silicone adhesive or mechanical attachment features such as small tabs with holes that receive barbs through the holes. The attachment is generally present at the top of the cutting element, leaving the bottom edge of the cutting element free from adhesive and able to come into direct contact with the lens capsule. The attachment also results in the cutting element being located concentric to the larger suction cup. The barbs in the tab holes allows for a small amount of freedom of movement of the cutting element, thus reducing distortion of the cutting element.

In the embodiment shown in FIG. 2C, the cutting element 222 is an electrical cutting element, though other cutting element designs are also possible, such as a mechanical cutting element with a sharp edge, or a combination of mechanical and electrical heat mechanisms in a cutting element. The anchored electrical leads 224 are visible in FIG. 2C, and are attached to the cutting ring 180 degrees apart, though other designs and positions of the electrical leads are also possible.

In other embodiments, the cutting element 222 can be mounted elsewhere on the suction cup other than what is shown in FIG. 2C, or mounted elsewhere on the capsulotomy device in relation to the suction cup. The cutting element 222 is configured to cut a portion of tissue (e.g. of the lens capsule).

In FIG. 2C, the cutting element 222 is a circular shape, but in other embodiments the cutting element can be rounded, elliptical, square, rectangular, irregular, or a different shape. The suction cup similarly can take on these shapes as well. The cutting element 222, like the suction cup 220, is collapsible. Thus, the cutting element 222 is composed of an electrically conductive, collapsible material (e.g., nitinol or other superelastic alloys) that can collapse for entry into the eye through the corneal incision, but can generally regain the shape it had prior to collapsing once it is inside the anterior chamber of the eye on the internal side of the cornea, allowing it to be used to cut or create an opening in the lens capsule of the eye. In some embodiments, the cutting element is inserted into a scleral incision instead of a corneal incision.

In use, suction is delivered via the suction tube 230 that is connected to the roof of the suction cup via an opening 226 in the roof. In some embodiments, the suction tube 230 includes a stem having a lumen through which suction can be applied to the suction cup 220. The opening 226 could be positioned in other locations on the suction cup 220, as well. Suction applied via the suction tube 230 evacuates the contents encompassed by the suction cup 220. This causes the suction cup 220 to push down against the lens capsule to form a vacuum seal with the sealing lip 226 of the suction cup 220 positioned against the lens capsule, thereby securing the suction cup against the lens capsule. In doing so, the suction cup 220 brings the bottom edge of the cutting element 222 into close contact with the lens capsule such that the entire 360 degrees of the cutting element 222 is in contact with the lens capsule. The electrical current discharge flowing into the device enters the cutting element via the leads 224 attached to the cutting element, in order to cut the tissue of the lens capsule along the circumference of the cutting element. When the cutting element 222 cuts a patch of the lens capsule, suction applied via the suction tube 230 can be used to retain the cut portion of tissue inside the capsulotomy device. Thus, allowing the removal of the device and cut portion of capsule tissue from the eye through the corneal incision. In order to gently release the suction cup, due to the adhesive characteristics of materials such as viscoeleastic, positive hydraulic pressure from the fluid filled line is used. By pushing the roller 134 of the roller dispenser 130 forward, the tubing is first pinched off and as the roller continues down the dispenser track, significant hydraulic pressure can be achieved. This hydraulic pressure forces fluid under the capsule of the eye and also releases the suction cup from the capsule. The roller dispenser is designed to deliver a small amount of pressured fluid, such as an amount between 0.02 ml and 1 ml.

Figure 2D:
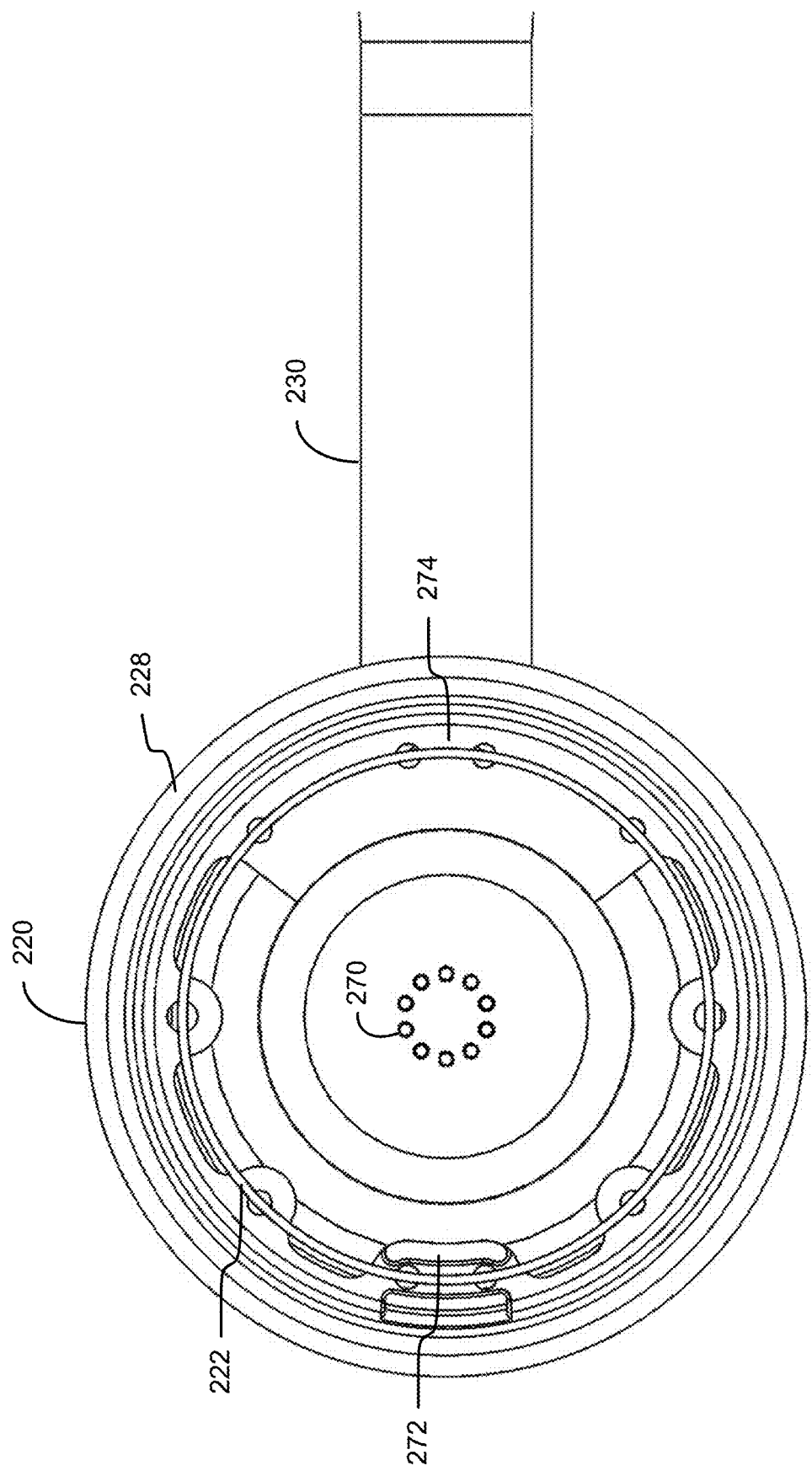
FIG. 2D illustrates a bottom view of a suction cup of a capsulotomy device, according to one embodiment.
Figure 2E:
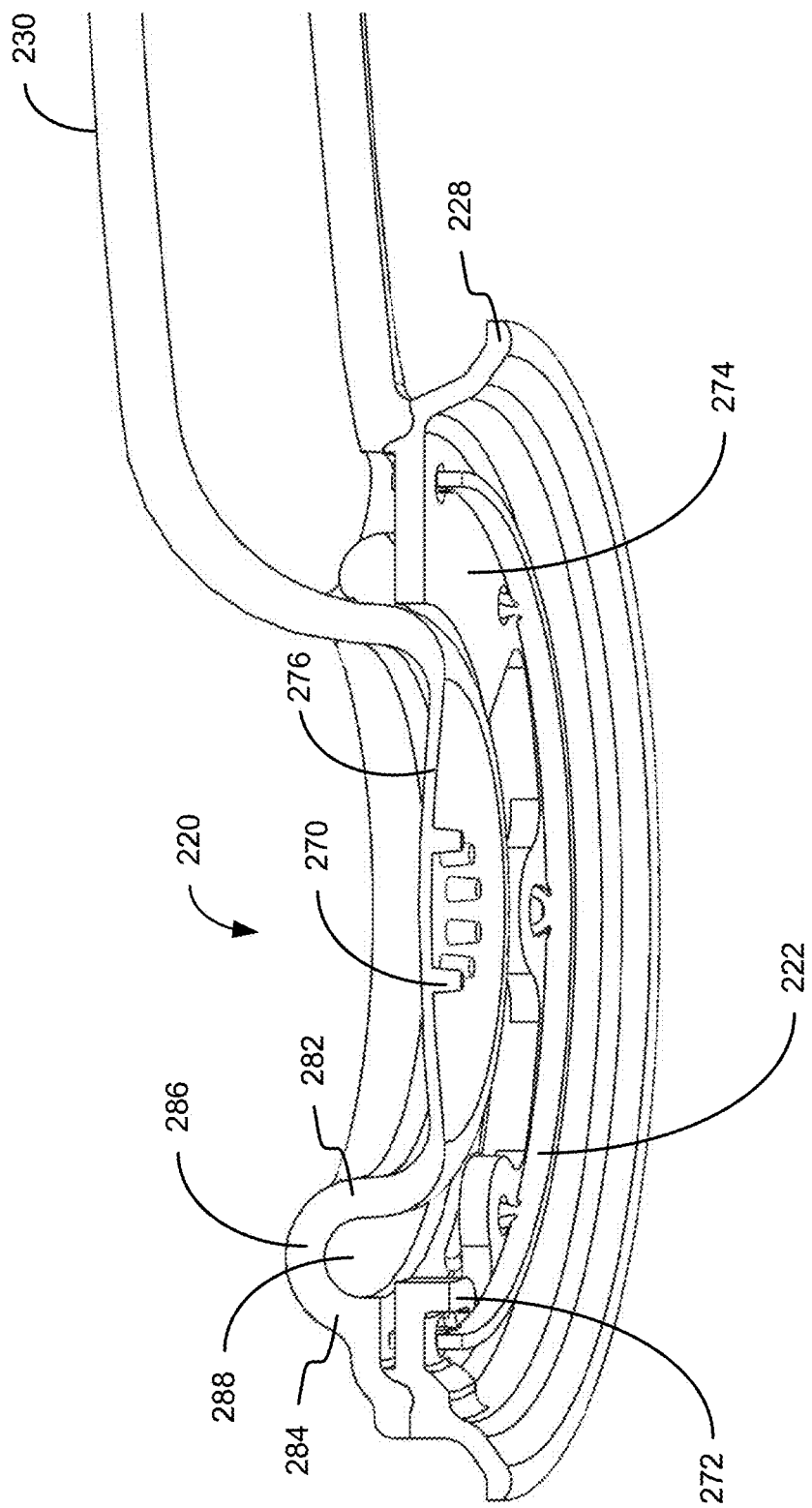
FIG. 2E illustrates a cross-sectional view of a suction cup of a capsulotomy device, according to one embodiment.

FIG. 2D illustrates a bottom view of a suction cup of a capsulotomy device, and FIG. 2E illustrates a cross-sectional view of a suction cup of the capsulotomy device, according to one embodiment. The suction cup includes multiple standoffs 270, a vertical wall 272, a baffle 274, and a sealing lip or skirt 228. Furthermore, the suction cup includes an inner wall 282, an outer wall 284, and a roof 286. The inner wall 282, outer wall 284, and roof 286 form a channel 288 that is in fluid communication with the suction tube 230.

In some embodiments, the standoffs are 0.006 inch tall and have tapered walls. In some embodiments, the standoffs 270 are disposed on a central membrane 276 that is connected to the inner wall 282 of the suction cup 220. The standoffs may be used to assist the alignment of the capsulotomy device to the visual axis once inserted into the eye of a patient. Furthermore, compression of the standoffs may be used to determine if suction pressure has been achieved by the suction cup 220.

The vertical wall 272 is used to provide a cushion between a push rod (not shown) and cutting element. When the push rod is slid forward to elongate the cutting element and suction cup for insertion into the eye, the vertical wall 272 is clamped between the push rod and cutting element so that the push rod does not impinge directly on the cutting element. In some embodiment, the vertical wall 272 is a silicone wall.

The baffle 274 equalizes the flow rate of fluid distribution within the suction cup going in or out of the suction tube 230. For example, as fluid is pushed out of the suction tube 230, the baffle 274 provides a path of fluid resistance that allows a first portion of the fluid to pass through the non-collapsing channel 288 and a second portion to go through holes in the baffle 274. This allows the fluid to be pushed out of the suction cup 220 along the entire circumference of the suction cup 220. The baffle 274 also equalizes the suction provided by the suction cup such that the suction is substantially similar long the circumference of the suction cup.

Cutting Element

Figure 3:
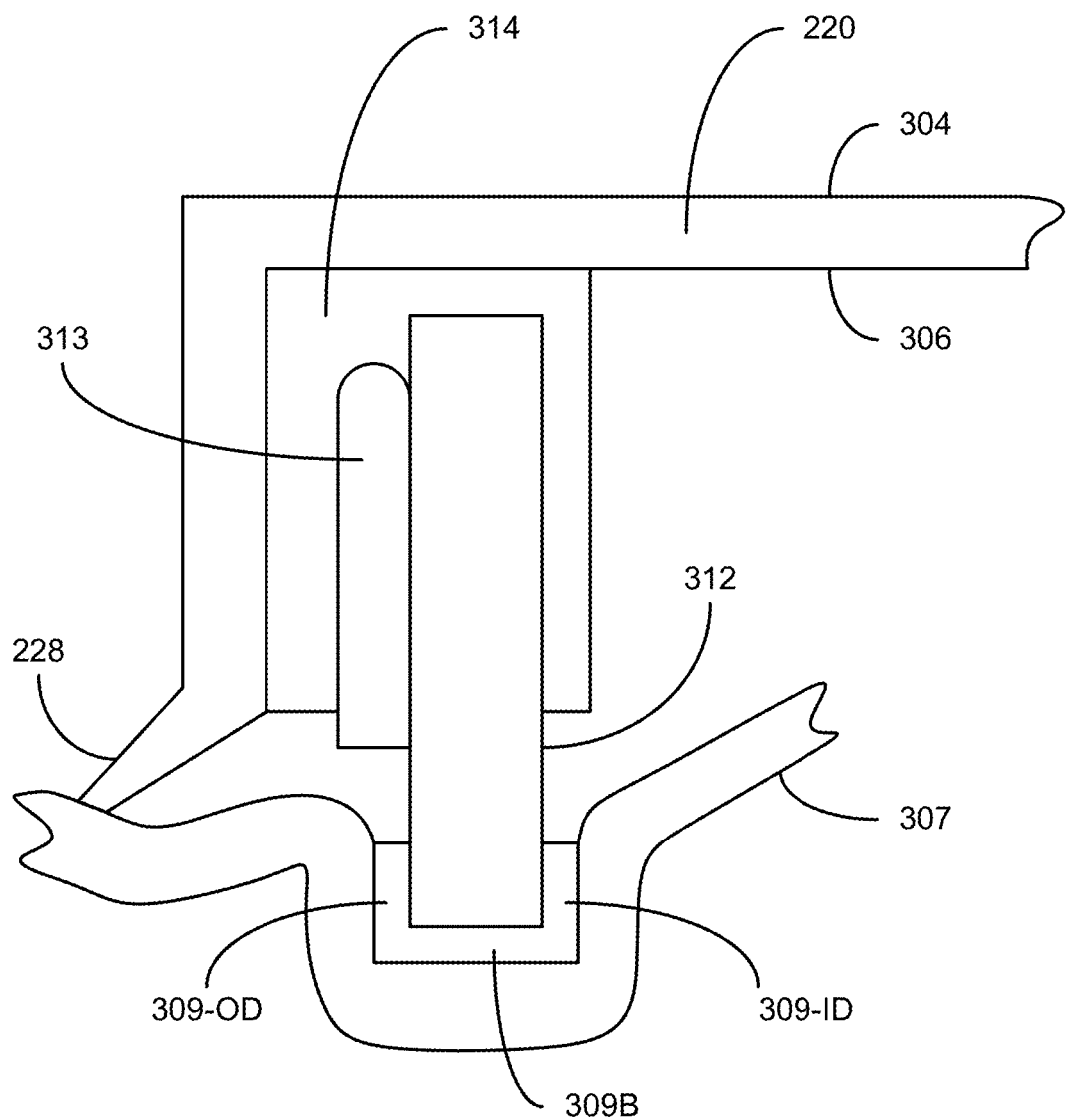
FIG. 3 illustrates a schematic cross-sectional view of the capsular membrane in contact with the cutting element and sealing lip of the microsurgery/capsulotomy device, according to one embodiment.

FIG. 3 shows a schematic cross section of the capsular membrane 307 forced by suction into intimate contact with the cutting element 309 (e.g., 309B, 309-OD (FIG. 3B), or 309-ID (FIG. 3B), and any combination thereof) and the sealing lip 228 of the suction cup 220. The cross section view of capsulotomy tip 210 shown in FIG. 3 includes a suction cup 220 having a roof 304, an underside 306 and a sealing lip 228, a cutting element having an elastically deformable ring 312 and an cutting element 309, and an electrical lead 313. In some embodiments, the cutting element 222 includes a coating or other structure along all or part of its surface to allow it to better adhere to the lens capsule to provide a uniform cut.

In the embodiment of FIG. 3, the cutting element 309 is mechanically supported by an elastically deformable ring 312, which is held to the suction cup 220 by potting material 314. In some embodiments, the cutting element 309 is placed along the bottom of the deformable ring 312, the inner diameter of the deformable ring 312, along the outer diameter of the deformable ring 312, or any combinations thereof. In some embodiments, the cutting element 309 is plated, electroplated, or sputtered onto the elastically deformable ring 312.

In some embodiments, the elastically deformable ring 312 is made of a conductive material. Furthermore, the elastically deformable ring 312 may be made of a material with a shape memory effect (SME) or superelastic property. For example, the elastically deformable ring 312 may be made of a nickel and titanium alloy (NiTi or Nitinol).

Electrical leads 313 bring electrical current to the cutting element 309. In some embodiments, the capsulotomy tip 210 includes multiple leads that connect to the deformable ring 312 or the cutting element 309 in multiple locations. The electrical leads 313 create a closed circuit between the cutting element 309 and a power supply or control unit (not shown) to provide electrical current to the cutting element 309.

In some embodiments, the cutting element 222 functions as a resistor. A very short electrical pulse quickly heats up the element (e.g., to greater than 500° C., such as 600° C., 700° C., 800° C., 900° C., 1000° C., 1200° C., 1500° C., and so forth). More than one pulse can also be delivered. In some embodiments, the heating process lasts for a few microseconds (e.g., 10 microseconds or less), though heating times can differ in other embodiments (e.g., 1 microsecond, 5 microseconds, 10 microseconds, 20 microseconds, 1 millisecond, 5 milliseconds, etc.). The duration of the electrical discharge is too short for heat to travel more than a few microns by conduction from the cutting element 222, so for a few microseconds, the thin layer of water that is trapped between the capsule and the cutting element 222, absorbs the energy of the discharge and forms steam. The steam expands and increases the tensile stress in the capsule enough to cleave it.

Since the electrical current is applied for only a few microseconds, tissue is not burned as it is with electrocautery instruments used in the past for performing capsulotomies. Due to this, the capsulotomy device 120 avoids the risks associated with burning tissue in a patient's eye, with possible collateral damage to nearby tissue, with lengthy application of heat, and other drawbacks. The energy of the cutting element 222 of capsulotomy device 120 is instead used to make a micro steam explosion to cleave the capsule, not burn it. In addition, the cutting element 222 of capsulotomy device 120 completes the severing of the tissue to free the severed piece from the capsule, unlike electrocautery devices that often only weaken the tissue and require tweezers to remove the severed piece. Further, in some embodiments, the cutting element has a mass of 0.35 milligrams or less, so bulky heating elements are not required as are commonly found with electrocautery instruments. The disclosed cutting method allows for minimal heat transfer to the capsule. The minimal heat allows for a shrinking of the collagen fibers and as a result of the shrinkage of the collagen, the capsular edge is slightly folded upward. This upward edge allows for the intraocular lens (IOL) to be firmly opposed the capsule edge thus preventing PCO.

Fluid Isolator and Roller Dispenser

Figure 4A:
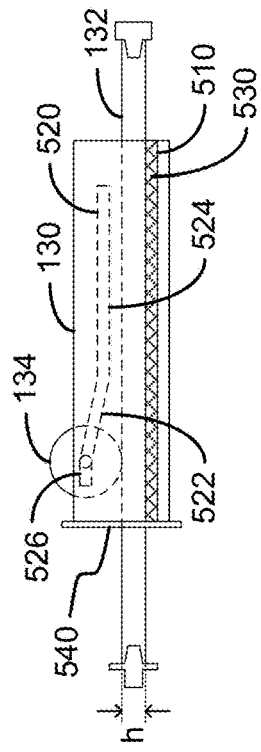
FIG. 4A through FIG. 4C illustrate cross-sectional views of the fluid isolator, according to one embodiment.
Figure 4B:
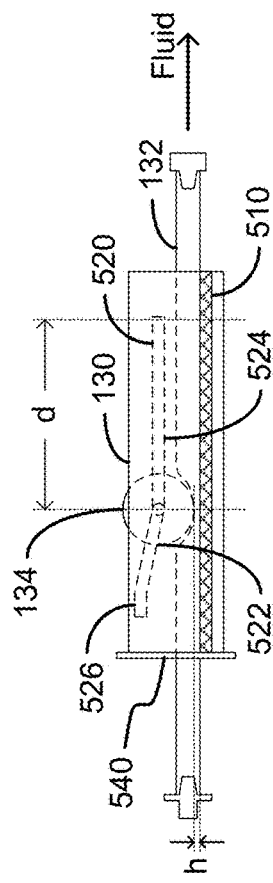
Figure 4C:
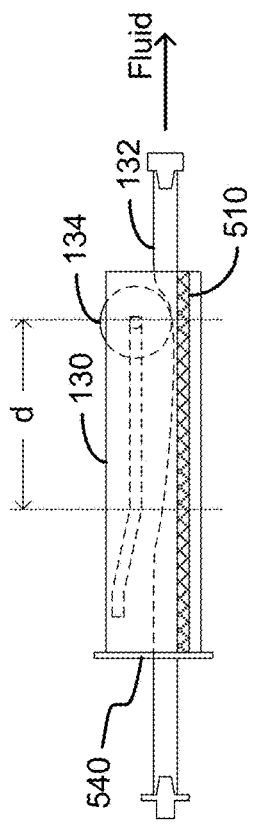

FIG. 4A through FIG. 4C illustrate cross-sectional views of the fluid isolator, according to one embodiment. FIG. 4A illustrates a cross-sectional view of the fluid isolator 140 when the fluid isolator is in an initial state. The fluid isolator has a first tube 410 (e.g., a PVC tube) that couples the console 110 to the vacuum end 144 of the fluid isolator 140, and a second tube 420 that couples the fluid end 142 of the fluid isolator to the capsulotomy device 120.

FIG. 4B illustrates a cross-sectional view of the fluid isolator 140 while suction is being applied by the console 110. As the console 110 applies suction through first tube 410, the vacuum formed due to the suction moves the floating piston 146 backwards, creating a vacuum in the fluid end 142. The vacuum created in the fluid end 142 draws fluid contained in the second tube 420 into the fluid end 142. As the fluid is drawn into the fluid end 142 of the fluid isolator 140, a vacuum is propagated through the second tube to the suction cup 220 of the capsulotomy device 120.

FIG. 4C illustrates a cross-sectional view of the fluid isolator 140 after maximum suction has been applied by the console 110. The piston 146 can travel from the front of the fluid isolator 140 towards the rear of the fluid isolator 140 until vacuum force is balanced on both sides of the piston. In some embodiments, the amount of vacuum the fluid isolator can apply is based on the total volume of the barrel 440 of the fluid isolator. In some embodiments, a 30 cc barrel is used for the fluid isolator 140. The fluid isolator is designed so that the barrel 440 does not significantly reduce in diameter under high vacuum as a reduction in diameter of the barrel 440 would cause increased friction between the floating piston and the barrel 440 of the fluid isolator. An increase in friction between the cylinder and piston would create an unequal amount of suction between the two chambers of the fluid isolator.

Figure 5A:
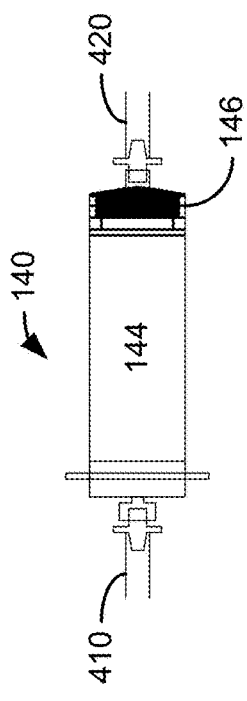
FIG. 5A through FIG. 5C illustrate a cross-sectional view of a roller dispenser, according to one embodiment.
Figure 5B:
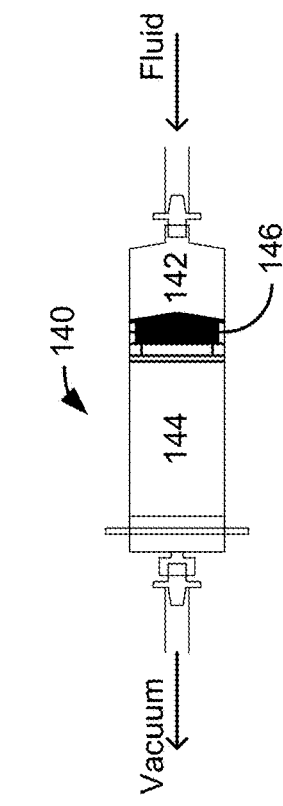
Figure 5C:
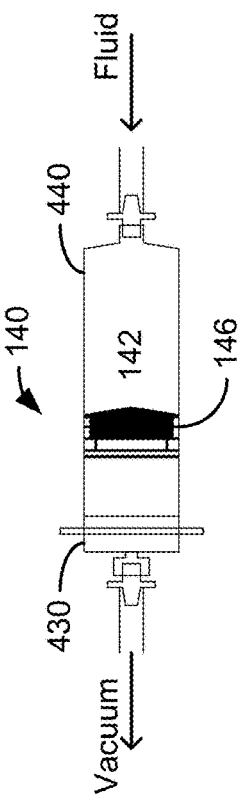

FIG. 5A through FIG. 5C illustrates a cross-sectional view of a roller dispenser, according to one embodiment. In some embodiments, the roller dispenser 130 is a modified roller clamp design that facilitates fluid delivery, with functionality similar to a peristaltic pump, described in detail with reference to FIG. 6. The conditions for fluid flow delivery, including amount of fluid delivered (e.g, between 0.02 ml and 1 ml), delivery time (e.g., between 0.1 seconds and 5 seconds), and speed and hydraulic pressure of the fluid, may be user-dependent.

FIG. 5A illustrates a cross-sectional view of the roller dispenser 130 in the open position. In the open position, the roller dispenser 130 does not restrict the flow of fluid to flow through the tube 132. In some embodiments, the roller dispenser 130 is in the open position when the roller 134 is at one extreme of the track 520 designed to guide the roller 134. In some embodiments, the track 520 is formed on one or two side surfaces of the housing 540 of the roller dispenser 130. In some embodiments, the track 520 if the roller dispenser 130 has a first non-sloped portion 526 where the gap h between the roller 134 and the bottom portion 510 of the roller dispenser is at its largest value, allowing fluid to freely flow through the tube 132. The track 520 of the roller dispenser 130 further has a sloped portion 522 that allows the roller 134 to clamp the tube 132. As the roller travels through the sloped portion 522 of the track, the gap h between the bottom potion 510 of the roller dispenser and the roller 134 decreases, pinching the tube closed and preventing the flow of fluid from flowing backwards through the tube 132. FIG. 5B illustrates a cross-sectional view of the roller dispenser 130 in an initial closed position.

After the roller 134 has pinched the tube 132 closed, as shown in FIG. 5B, if the roller 134 advanced further along a third portion 524 of the track 520, the fluid that is inside the tube 134 is pushed in the direction of the movement of the roller 134 as shown by the arrow of FIG. 5B. After the roller 134 has been advanced a full stroke (i.e., the entire travel of the track) as shown in FIG. 5C, the volume of fluid that was contained in the portion d of tube 132 is pushed forward along the tube and released out via the suction cup 220 of the capsulotomy device 120. For example, if the inner diameter (ID) of the tube is 3.2 mm, and the full travel of the roller dispenser (d) is 2.5 cm, then the volume of fluid (v) pushed by the roller 134 is substantially equal to:

$$v = \pi (ID/2)^2 \times d = \pi (0.16 \text{ cm})^2 \times 2.5 \text{ cm} = 0.2 \text{ ml}$$

In some embodiments, the roller dispenser is designed such that the amount of fluid to be pushed out by the roller 134 is between 0.02 ml to 1.0 ml, and the time to push out fluid is between 0.1 and 5 seconds. In some embodiments, the roller dispenser is designed such that the amount of fluid to be pushed out by the roller 134 is between 0.1 ml to 1.0 ml. The liquid pushed by the roller dispenser 130 travels through tube 132 such that a substantially equal amount of fluid is expelled into the suction cup 220 of the capsulotomy device 120. The fluid delivered the suction cup 220 of the capsulotomy device 120 aids in detaching the suction cup 220 from the lens capsule of the eye of a patient. If the amount of fluid and pressure of the fluid, is below the minimum thresholds, the pressurized fluid might not be capable of detaching the suction cup 220 form the lens capsule of the eye. If the fluid is above a maximum threshold amount, the suction cup will be released from the capsule of the eye and simultaneously, the excess fluid will flow out through the corneal incision.

In some embodiments the roller dispenser 130 has a compliant surface 530 disposed on the bottom portion of the roller dispenser. In some embodiments, the compliant surface 530 is composed of a foam material to allow the roller 134 to be advanced along the second portion 524 track 520 after the tube has been pinched off. In some embodiments, the compliant surface 530 is stiff enough to keep the tubing pinched off, while allowing travel to push fluid down the tubing. In some embodiments, the compliant surface 530 is composed of a soft material that allows the compliant surface 530 to be compressed by a force exerted when the roller 134 is clamping the tube 132. In addition to foam for the compliant surface, a compliant surface can be created by having a surface opposite the tube that deflects such as the inner surface of the roller dispenser housing. In addition, a plastic or metal leaf spring can be used instead of foam. Additional features incorporated in the foam, leaf spring or housing can be utilized in order to provide for additional fluid dispensing characteristics.

FIGS. 4A through 4C illustrate one design of a fluid isolator type mechanism. FIGS. 5A through 5C illustrate one design of a fluid delivery mechanism, specifically via a roller dispenser design. Other embodiments of fluid delivery mechanisms are shown in FIGS. 21 and 22.

Figure 21:
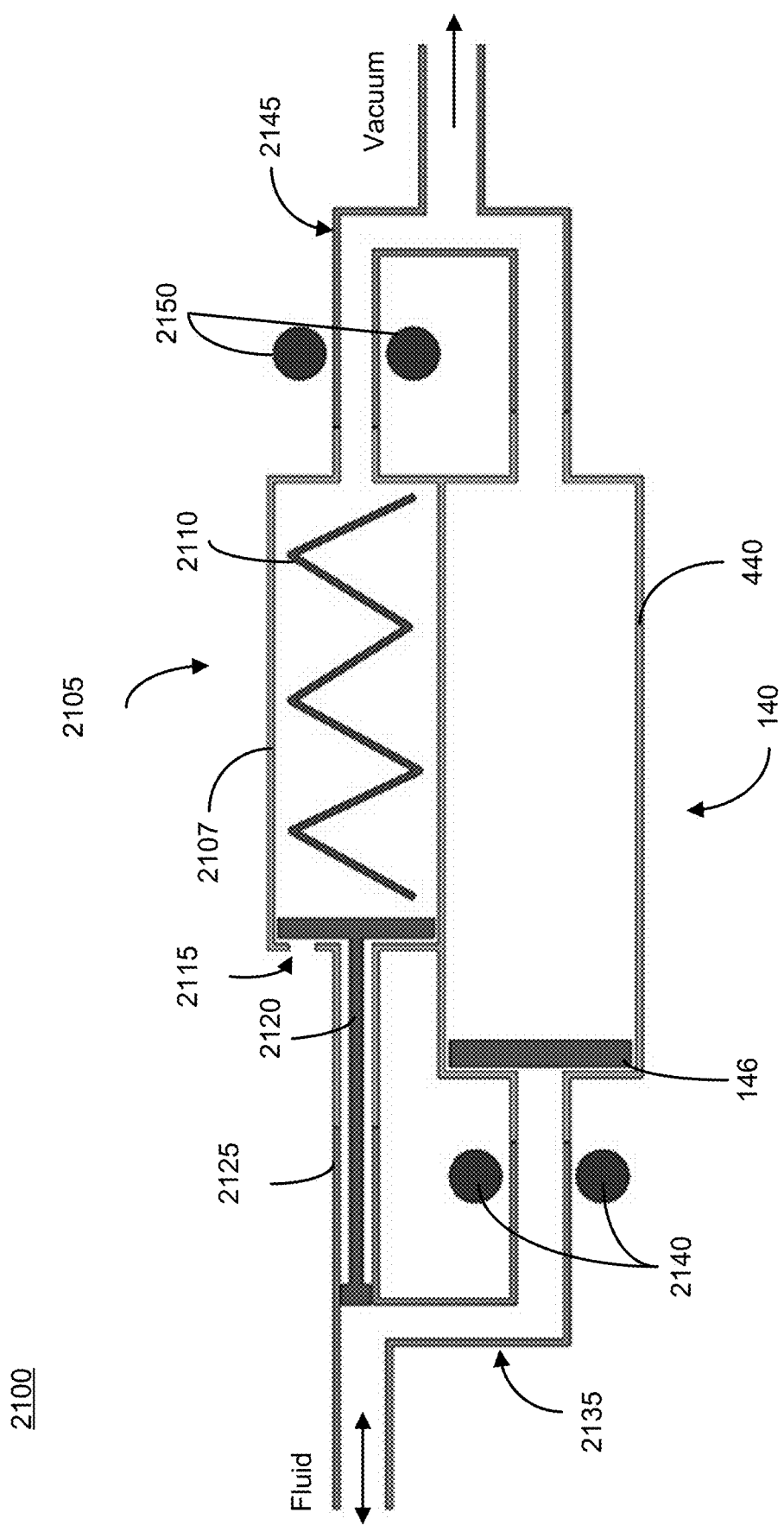
FIG. 21 illustrates an embodiment of a fluid flow delivery mechanism with a spring-loaded cylinder, according to one embodiment.

Referring to FIG. 21, FIG. 21 illustrates an embodiment of a fluid flow delivery mechanism with a spring-loaded cylinder, according to one embodiment. A spring-loaded cylinder 2105 is coupled in parallel to a fluid isolator 140 via the capsulotomy device 120 and the console 110. The barrel 2107 of the spring-loaded cylinder 2105 includes a piston 2120 to deliver fluid to the capsulotomy device 120, a spring 2110, and a vent 2115, and is attached to the fluid end of the capsulotomy device 120 via a syringe 2125. Pinch clamps, e.g., pinch clamps 2140 and 2150, are located on a fluid suction line 2135, which connects the fluid isolator 140 to the handpiece, and on the cylinder release line 2145, which connects the spring-loaded cylinder 2105 to the vacuum on the console 110.

When the spring 2110 is in an uncompressed state, fluid fills the fluid suction line 2135 such that no air is trapped in the syringe 2125. To provide enough pressure to compress the spring 2110 and fill the syringe 2120 with fluid for fluid delivery, the pinch clamps 2140 on the fluid suction line 2135 are pressed and the applied vacuum from the console 110 is increased. The pinch clamps 2150 on the cylinder release line 2145 are pressed to hold the vacuum in the spring-loaded cylinder 2105 and keep the spring 2110 compressed. The pinch clamps 2140 pressing the fluid suction line 2135 are released and suction is applied until 21.7 cc of air at 0.3 atm is trapped in the fluid isolator 140. The pump line is vented through the vent until atmospheric pressure is reached and the tubing returns to its original diameter. If the pump line is not vented, the expanded diameter may consume a significant portion of the fluid in the syringe 2125. The pinch clamps 2140 on the fluid suction line 2135 are pressed to prevent fluid from entering the fluid isolator 140. The pinch clamps 2150 on the cylinder release line 2145 are released to decompress the spring 2110 and deliver fluid to the capsulotomy device 120.

Figure 22:
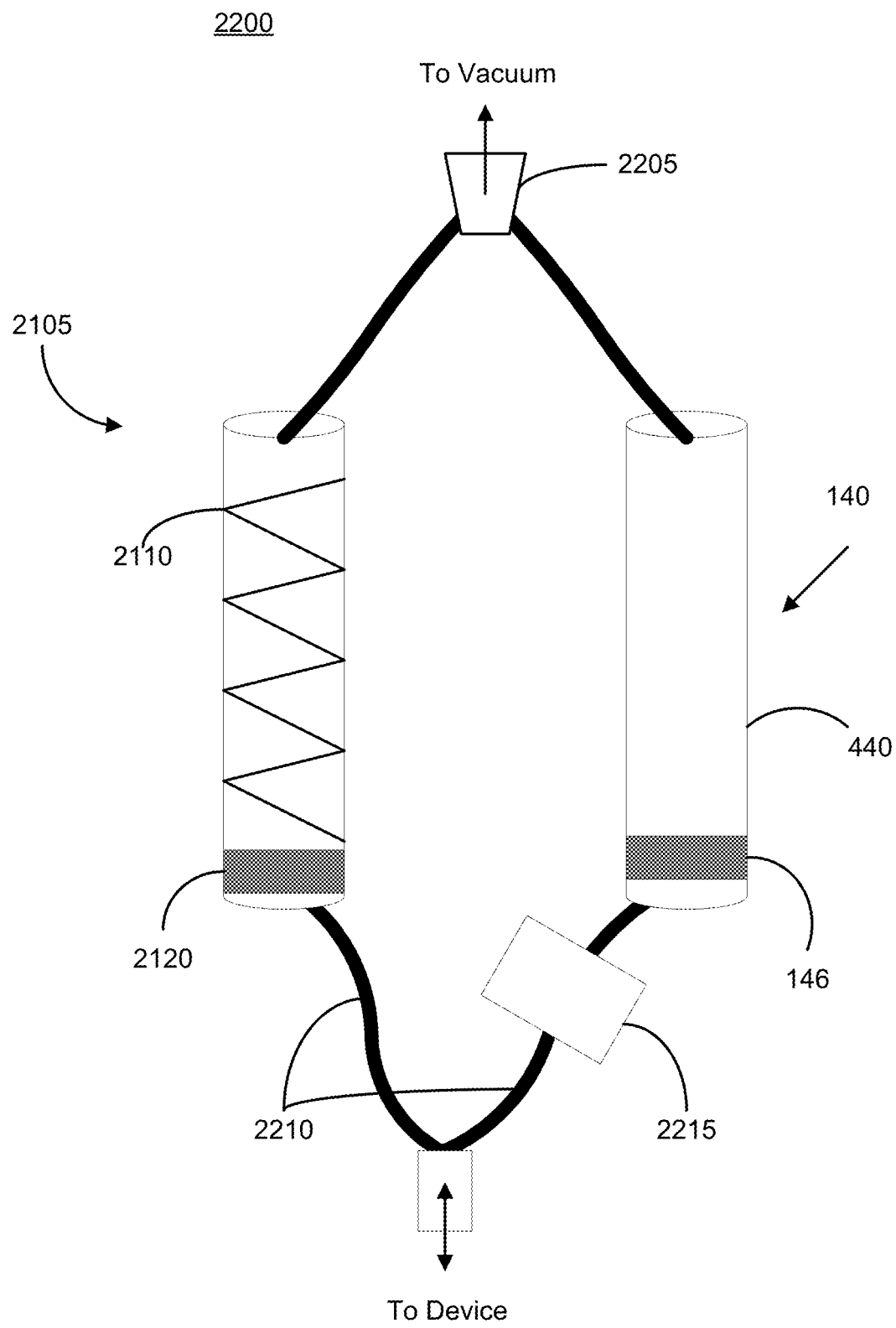
FIG. 22 illustrates another embodiment of a fluid flow delivery mechanism with a spring-loaded cylinder, according to one embodiment.

Referring to FIG. 22, FIG. 22 illustrates another embodiment of a fluid flow delivery mechanism with a spring-loaded cylinder, according to one embodiment. A spring-loaded cylinder 2105 and fluid isolator 140 are connected to the capsulotomy device 120 and the console 110 via a luer fitting 2205. The spring-loaded cylinder 2105 contains a spring 2110 that is compressed in order to dispense fluid into the capsulotomy device 120 and release the suction cup 220 and a piston 2120 to compress the spring 2110. The fluid isolator includes a barrel 440 and a piston 146. A check-valve 2215 monitors the direction of fluid flow along the device lines 2210 between the fluid isolator 140 and the capsulotomy device 120. The dual cylinder assembly (i.e., the spring-loaded cylinder 2105 and the fluid isolator 140) are held to the console vertically via a wye ("Y" connector).

To prime the fluid flow delivery mechanism 2200, the capsulotomy device 120 is submerged in a beaker of fluid and vacuum is initiated. The check value 2215 ensures that the fluid is flowing towards the fluid isolator. The device line 2210 requires approximately 6 ml of fluid to fill the line. Once the device line 2210 is filled, the vacuum on the console 110 is stopped and held. The floating piston 146 requires sufficient unused travel within the barrel 440 to utilize the remaining travel of the floating piston 146 and create additional vacuum for the capsulotomy device 120.

The user places tip of the capsulotomy device 120 in an eye, and positions the suction cup over the visual axis and initiates the vacuum of the console 110 to press the suction cup 220 and cutting element against the capsule of the eye. Once vacuum is achieved, the cut discharge is initiated.

After the lens capsule is cut, the vacuum is released and the spring-loaded cylinder 2105 dispenses the fluid in the device line 2210 in order to release the suction cup 220 from the eye. The capsulotomy device 120 can then be removed from the eye.

Figure 6A:
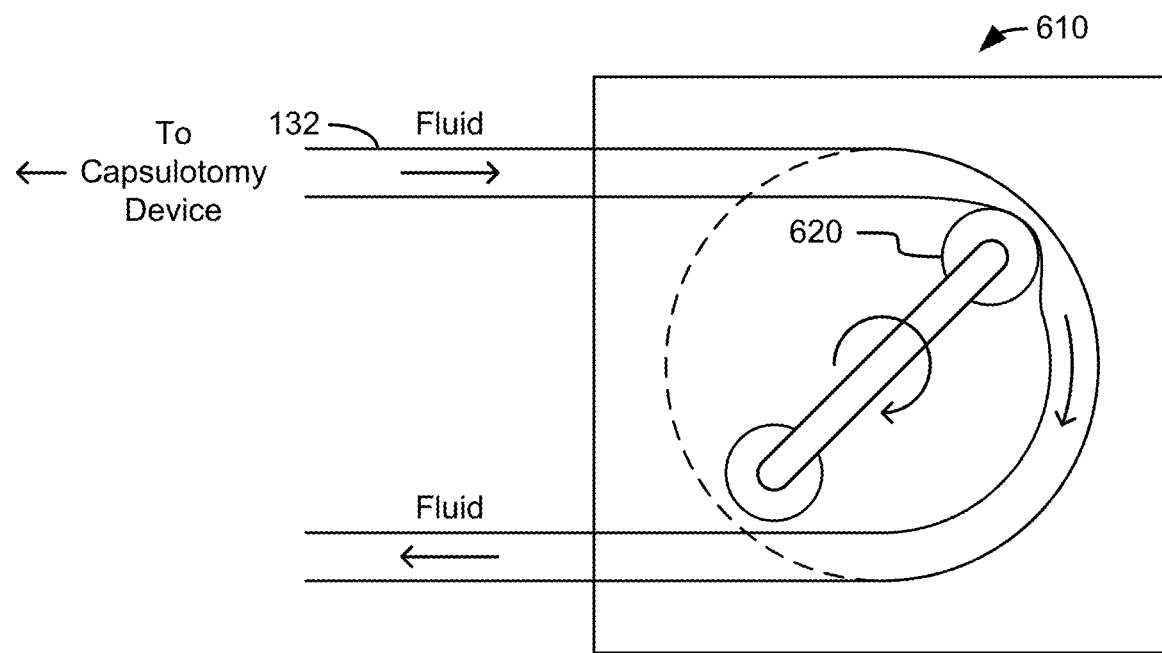
FIG. 6A and FIG. 6B illustrate a cross-sectional view of a peristaltic pump, according to one embodiment.
Figure 6B:
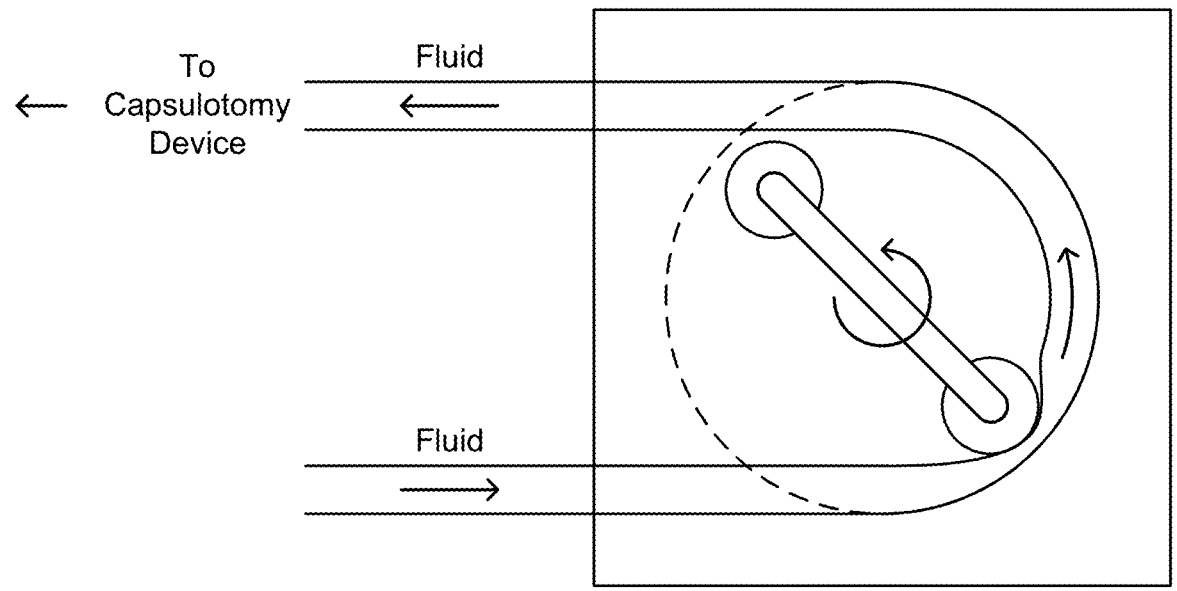

Other designs of fluid delivery mechanisms include the use of a peristaltic pump incorporated in the console, as shown in FIGS. 6A and 6B. The peristaltic pump may enable the reduction in the complexity of the disposable capsulotomy system 100. For example, if a peristaltic pump is used, the suction of the fluid provided by the fluid isolator can be achieved by operating the peristaltic pump in a first direction (FIG. 6A), and the dispensing of the fluid provided by the roller dispenser can be achieved by operating the peristaltic pump in a second direction (FIG. 6B). As illustrated in FIGS. 6A and 6B, the peristaltic pump 610 includes a set of rollers 620 that rotate along an axis of rotation. As the rollers 620 rotate, the rollers 620 compress the tube 132, pushing a fluid that is inside the tube 132 along the direction of rotation of the rollers 620. When the direction of rotation of the rollers 620 is opposite to the end connected to the capsulotomy device, the peristaltic pump 610 provides suction to the capsulotomy device. When the direction of the rotation of the rollers 620 is towards the end connected to the capsulotomy device, the peristaltic pump 610 dispenses an amount of fluid proportional to the amount of rotation of the rollers 620. In one embodiment, a device with a peristaltic pump includes a syringe attached to the fluid line to more easily determined the applied suction pressure. After priming the syringe, the syringe will contain around 6.5 cc of trapped air. Suction is applied such that the trapped air expands by a factor of 3.34, e.g., around 21.7 cc, indicating an applied suction pressure of 21 Hg is reached.

Prevention of Posterior Capsule Opacification

Posterior capsule opacification (PCO), also referred to as "secondary cataract" or "after cataract," develops over the clear posterior capsule a few months to a few years after an uneventful cataract surgery. PCO results from the growth and abnormal proliferation of lens epithelial cells (LECs) on the capsule that may have been missed in the process to remove the LECs at the time of cataract surgery. The LECs migrate to the posterior capsule where they approach the central visual axis and cause visual axis obscuration, resulting in dimness of vision. The LECs that are the most biologically active and are known to cause PCO reside in the capsular fornix, making them difficult to remove. Specifically, after a capsulotomy is performed, the cataractous lens inside the lens capsular bag is removed. The LECs can be attached to the posterior surface of the capsular bag, and can remain in the empty bag following removal of the cataractous lens. The new artificial lens is then placed inside the capsular bag, but the LECs may remain on some surface of the bag. Their abnormal proliferation can cover the inner surface of the posterior area of the capsule, forming a secondary cataract or a posterior opacification on the new artificial lens that then must be treated in the patient. The invention described herein provides a variety of ways to prevent or reduce occurrence of PCO, or to reduce the amount of opacification that may occur. For example, the invention uses procedures that can kill, damage, flush, or otherwise remove or at least reduce the LECs in the bag during performance of the capsulotomy (or at another point in the surgical procedure) so that there are no LECs or a reduced number of LECs that remain upon insertion of the new lens, thus preventing or reducing PCO. In particular, the device uses a fluid flush that surges fluid between the capsule and lens cortex because the cleavage plane has less fluid resistance than the dissection plane between the eye capsule and the suction cup. In doing so, the fluid flush achieves hydrodissection of the lens, i.e., separating the lens cortex from the bottom surface of the capsule. The surge of fluid occurs substantially 360 degrees simultaneously thus also encouraging complete removal of all lens epithelial cells. The surge cleaves the attachments of the LECs from the lens capsule and allows the removal of the LECs during subsequent normal irrigation and aspiration.

Moreover, following a conventional capsulotomy, a wound healing response is triggered to repair the severed tissue. A typical corneal wound healing cascade is complex and involves stromal-epithelial and stromal-epithelial-immune interactions mediated by cytokines. Keratocyte apoptosis is the earliest stromal event noted following epithelial injury and remains a likely target for modulation of the overall wound healing response. Other processes such as epithelial mitosis and migration, stromal cell necrosis, keratocyte proliferation, myofibroblast generation, collagen deposition, and inflammatory cell infiltration contribute to the wound healing cascade and are also likely modulated by cytokines derived from corneal cells, the lacrimal gland, and possibly immune cells. The wound healing response oftentimes causes fibrosis to form around the edge of the capsulotomy. This fibrosis formed around the capsulotomy can impact in the proliferation of epithelial cells causing an opacification of the posterior capsule.

Some embodiments of the disclosed capsulotomy device provide a precise cut in the capsule of a patient, reducing the likelihood of a wound healing response from triggering in the patient. For example, the precise cut occurs due to the design of the capsulotomy device, at least because of the electrical cutting element design in which a short electrical pulse quickly heats up the element to cause the tear in the tissue resulting in an opening formed in the lens capsule. In addition, the suction cup design can contribute the precise cutting ability of the device since it stabilizes the cutting element against the tissue to allow a clean cut to occur with a clean edge around the capsulotomy opening. As a wound healing response is not triggered after the performance of a capsulotomy, a fibrosis is not formed around the capsulotomy. Thus, this reduces the likelihood of PCO occurring after the performance of the capsulotomy.

Figure 7:
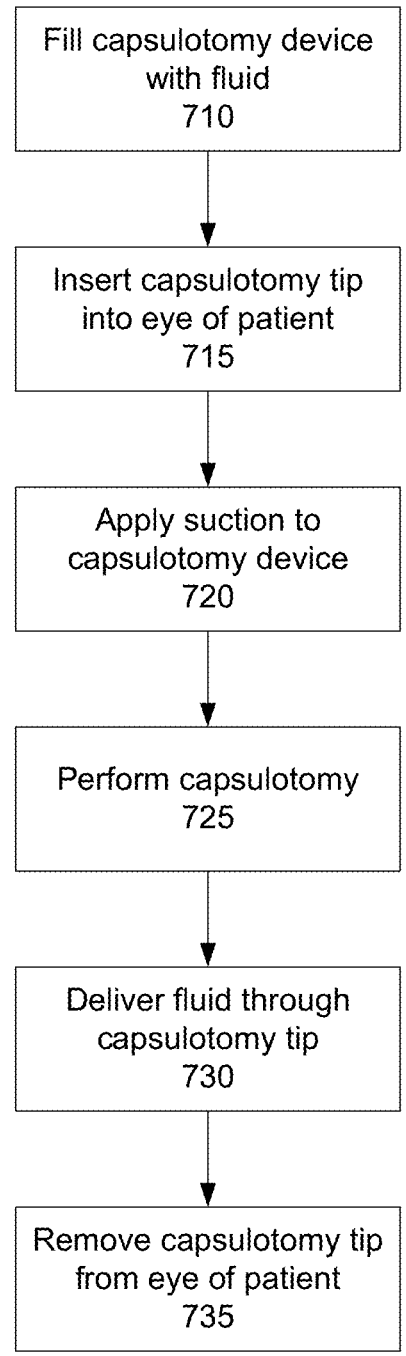
FIG. 7 illustrates a flow diagram for the operation of the capsulotomy systems, according to one embodiment.

FIG. 7 illustrates a flow diagram including steps that provide PCO prevention/reduction, specifically the operation of the capsulotomy systems that result in PCO prevention/reduction, according to one embodiment. This example refers to a capsulotomy device, but the device does not have to be capable of performing a capsulotomy, but can be a device that has some subset of the components and capabilities described below. Similarly, capsulotomy device 120 is used as an example, but other capsulotomy devices can be used to perform the method or perform a subset of the steps of the method described below.

The capsulotomy device 120 is filled 710 with fluid (e.g., balanced salt solution (BSS), viscoelastic gel (visco), sterile water, or a combination thereof). The fluid can be contained within a lumen within the device, such as within tube 132. In some embodiments, the fluid enters the device through the capsulotomy tip 210. In particular, the fluid can be added through the suction cup 220 of the capsulotomy tip 210. In some embodiments, the capsulotomy device 120 is filled with fluid by placing the capsulotomy tip 210 inside a beaker with the fluid, attaching a syringe to the end of the tube of the capsulotomy device, and drawing the plunger of the syringe. In some embodiments, the roller dispenser 130 is attached to the capsulotomy device 120 prior to filling the capsulotomy device with fluid. In some embodiments, the device 120 is filled with fluid via a fluid reservoir that is attached to the device. The reservoir may remain attached to the device during surgery or may be removed.

In some embodiments the capsulotomy device is filled with fluid prior to connecting the capsulotomy device 120 to the console 110. In another embodiment, a peristaltic pump is built into the console, and it automatically primes the line after it is placed in the console. Once the capsulotomy device 120 is filled with the fluid, the capsulotomy device 120 can be connected to the console via the fluid isolator 140. In other embodiments, the capsulotomy device 120 is connected to the console 110, and the console 110 performs the steps to fill the capsulotomy device 120 with fluid.

The capsulotomy tip 210 is inserted 715 into the eye of a patient. The capsulotomy tip 210 is inserted into the eye of the patient through a corneal incision by collapsing the capsulotomy tip 210 to reduce the width of the capsulotomy tip 210 prior to inserting the capsulotomy tip into the eye of the patient. After the capsulotomy tip 210 has been inserted into the eye of the patient, the collapsed capsulotomy tip 210 is expanded until the capsulotomy tip 210 generally regains the shape it had prior to collapsing.

Suction is applied 720 to the capsulotomy device 120. In some embodiments, suction is applied by the console 110 in response to a button being pressed in the console 110. The suction is applied through a fluid isolator 140 to prevent the fluid inside the capsulotomy device from entering the pump providing the vacuum. Suction is applied to the capsulotomy device 120 to secure the capsulotomy tip 210 to the lens capsule of the patient. In doing so, the cutting element 222 of the capsulotomy device 120 is placed in close contact with the lens of the patient.

In some embodiments, the suction that secures the suction cup 220 to the eye of the patient causes stress in the capsule of the eye, thus killing or removing some epithelial cells attached to the interior surface (that is, the inner surface) of the capsule of the eye of the patient. For example, this stress or shear force placed on the capsule can cause a slight temporary change in the shape of the lens capsule or a movement of the lens capsule that releases or affects the viability of the epithelial cells. In addition, the tearing and separation of the portion of tissue and/or the attachment of the portion of tissue to one or more surfaces of the suction cup for removal can similarly cause a movement or change in shape that releases or damages the epithelial cells. If released, the epithelial cells may be flushed, such as by the process described below. If injured, the cells may be unable to abnormally proliferate, and thus cannot cause the opacification or at least can cause less opacification. In some embodiments, the suction cup 220 applies a vacuum of 21 inches of mercury.

A capsulotomy is performed 725 using the capsulotomy device 120. The capsulotomy is performed by providing a preset electrical current or voltage to an electrical cutting element of the capsulotomy tip 210. As such, the electrical cutting element can cut the lens capsule along the circumference of the cutting element 222. In some embodiments, the electrical pulse applied by the cutting element 222 of the capsulotomy device creates mechanical shock waves from the microsteam explosions that kills or removes some epithelial cells in the posterior capsule of the eye of the patient.

Fluid is delivered 730 or advanced through the capsulotomy tip. In some embodiments, the fluid delivered is a balanced salt solution (BSS), viscoelastic gel (visco), sterile water, a hypo-osmotic fluid that will lyse cells, a substance that causes toxicity in lens epithelial cells, or a combination thereof In some embodiments, the fluid is pushed through the suction cup 220 of the capsulotomy tip 210 by advancing the roller 134 of the roller dispenser 130 a full stroke to push a set amount of fluid along the tube 132. The fluid that is pushed through the suction cup performs at least two functions. First, the fluid helps detach the suction cup from the eye of the patient. In particular, the fluid helps the lip 228 of the suction cup to detach from the lens capsule of the eye of the patient. For instance, an ophthalmic viscosurgical device (OVD) or a viscoelastic fluid may be used during the procedure to stabilize the anterior chamber of the eye. This OVD may cause the suction cup 220 to stick to the capsule of the eye, even after suction has been released from the suction cup. Thus, the pressure of the fluid being expelled from the suction cup creates a force that detaches the suction cup 220 from the capsule of the eye of the patient. Also, the fluid reduces the likelihood of the capsulotomy patient from experiencing PCO by forcing fluid around the lens to the posterior area of the capsular bag thereby flowing past the anterior half of the lens where the epithelial cells are located or attached to the capsular bag, and washing them way, creating a shearing effect, or damaging or killing some epithelial cells as described herein below in conjunction with FIG. 8. The fluid is contained in a sealed environment or sealed bag that is created by attachment of the suction cup to the lens capsule. Thus, the fluid can flow around the nucleus within the sealed environment with some force such that the nucleus is typically broken free or hydrodissected from the capsule, and the fluid can release the epithelial cells and/or can flush or cleanse or possibly damage the epithelial cells that remain. In some embodiments, a fluid that kills human cells on contact, such as sterile water, is used. In this embodiment, the fluid may be left in contact with the LECs for several minutes to allow the fluid to kill the LECs. OVD may insulate the cells of the eye outside of the capsule and thereby preventing any damage to these cells. During the several minutes after the fluid surge by the fluid, the fluid is diluted with intracellular ions released by nearby damaged cortical cells thereby decreasing its toxicity of the fluid.

Figure 8A:
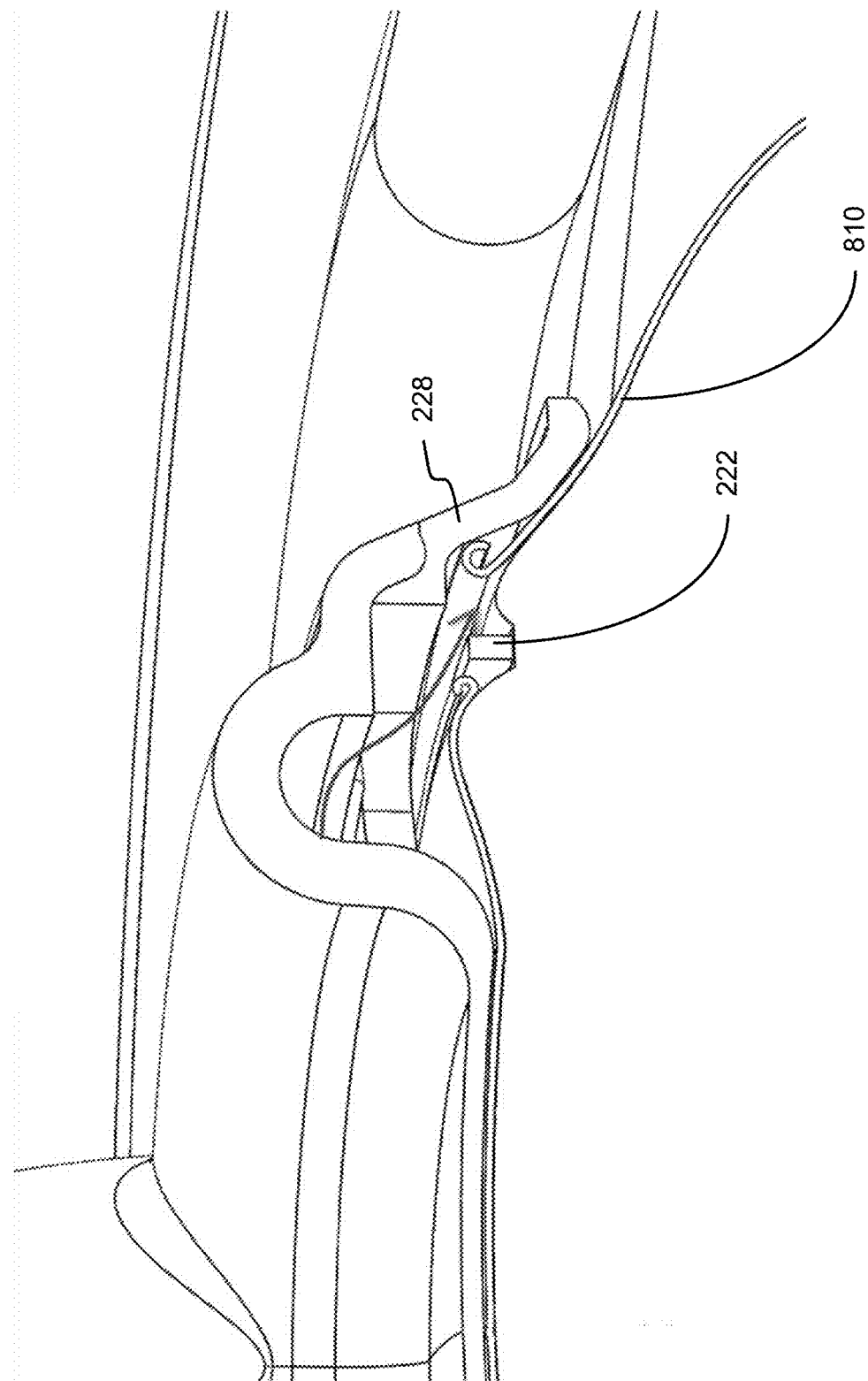
FIG. 8A illustrates a diagram indicating the flow of fluid during the release of the suction cup, according to one embodiment.

A portion of the fluid that is pushed through the suction cup 220 of the capsulotomy device 120 is pushed underneath the lens capsule, through an opening in the lens capsule formed when the cutting element 222 performed a cut along the circumference of the cutting element, as illustrated in FIG. 8A. The fluid that is pushed underneath the lens capsule hydrodissects the capsule of the eye, thus removing or killing some of the epithelial cells during the process. Since the fluid is delivered by a suction cup, the fluid can spread across the cup down the walls, and enter the capsular bag around the circumference of the capsulotomy. In this manner, the fluid can be delivered in 360 degree fashion such that the lens inside the bag is surrounded or engulfed in the fluid, resulting in effective removal of the epithelial cells that receive fluid on all sides. The fluid travels 360 degrees around the lens from the anterior to the posterior of the lens, as opposed to what might happen if a single stream or jet of fluid were delivered into the opening, which would travel along one side of the lens from the anterior to the posterior and then return to the anterior on the opposite side of the lens. In other words, the stream of fluid would travel around the lens in one direction, while the suction cup, in contrast, has a fluid delivery structure that forces a flow that surrounds the lens in all directions, with the fluid meeting in all directions on the posterior surface of the capsule to cause a more vigorous flushing at the posterior. Because of the inertia and viscosity of the surrounding medium, the faster the fluid flow is executed, the greater the hydrodynamic stress on the LEC.

In some embodiments, the suction cup 220 has stiff walls such that a fluid delivered through the suction cup during a capsulotomy procedure does not cause the suction cup 220 to expand. Furthermore, the suction cup 220 has a low profile or volume, such that the path of least resistance for the fluid being delivered through the suction cup is the plane between the bottom surface of the capsule and the lens cortex (the subscapular plane).

Figure 8B:
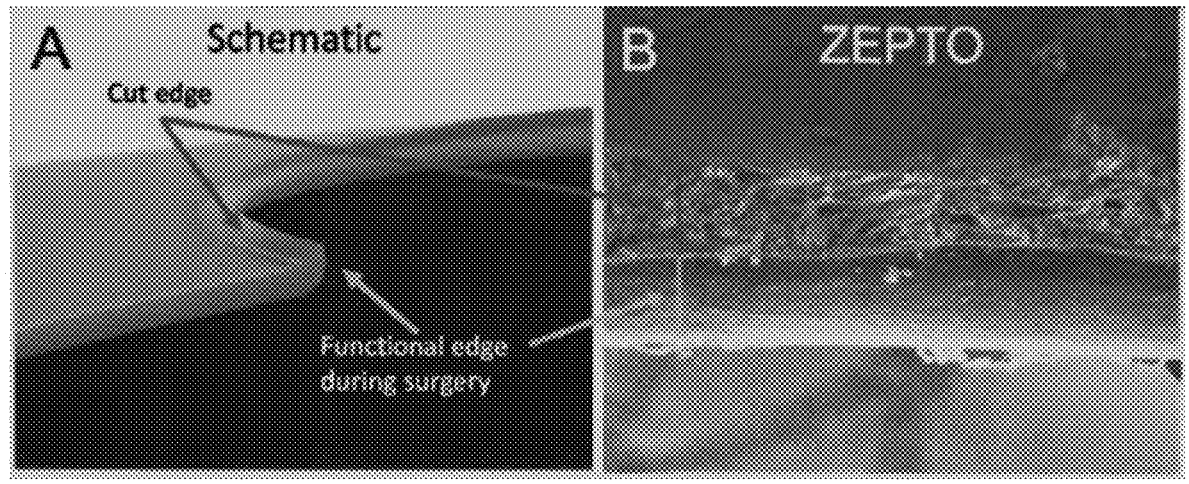
FIG. 8B illustrates the cut and curled capsulorhexis edge generated by the capsulotomy, according to one embodiment.
Figure 8C:
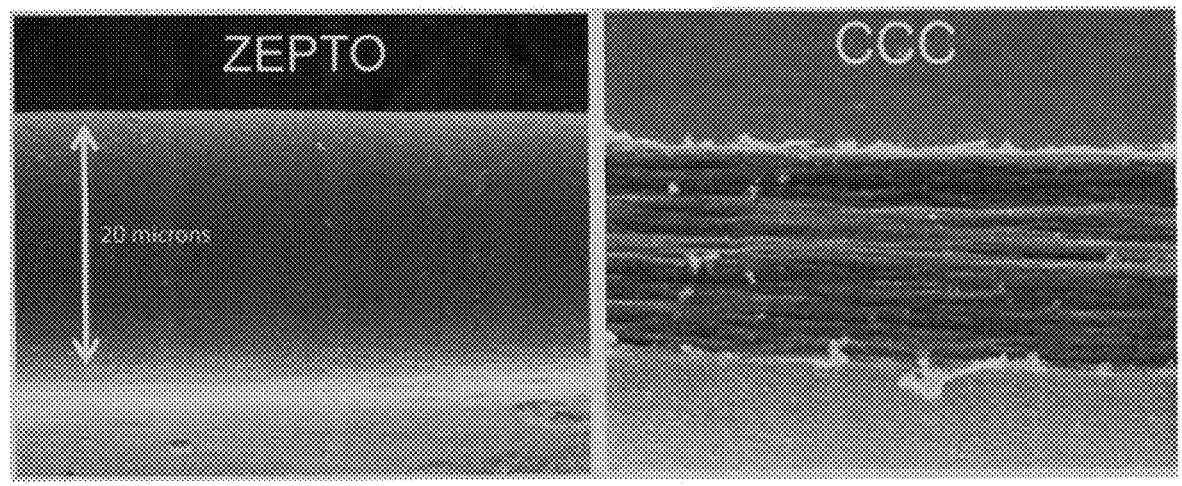
FIG. 8C illustrates a scanning electro-micrograph (SEM) of the side view of the curled capsulorhexis edged generated by the capsulotomy device and a cut edge from a continuous-tear curvilinear capsulorhexis (CCC), according to one embodiment.

In some embodiments, after being cut, the lens capsule 810 curls around the cut edges as illustrated in FIG. 8A. FIG. 8B illustrates the cut and curled capsulorhexis edge generated by the capsulotomy, according to one embodiment. It shows a schematic of a cut on the left (A) including the functional edge during surgery, and a cut using the capsulotomy device on the right (B) including the curled edge. FIG. 8C illustrates a scanning electro-micrograph (SEM) of the side view of the curled capsulorhexis edged generated by the capsulotomy device (left) and a cut edge from a continuous-tear curvilinear capsulorhexis (CCC) (right), according to one embodiment. As shown in FIG. 8C, the cut from the CCC has a rough edge that can impact in the proliferation of epithelial cells causing an opacification of the posterior capsule. In contrast, the cut performed with the disclosed capsulotomy device has a curled edge that is believed to aid in the prevention of epithelial cells from proliferating, preventing the occurrence of PCO.

The curled edges form a converging fluidic inlet under the rolled edge that helps guide the fluid to flow between the inner surface of the capsule and the outer surface of the lens, thereby impinging directly on the LEC, thus allowing the fluid pressure to damage or remove the epithelial cells that are located in that part of the eye. The curling of the edges of the capsule can be formed due to the thermal gradient from the electrical discharge of the device, specifically as a result of the heat created, as a result of the one or more steam explosions that can occur as described above, or due to some other factor associated with the electrical discharge.

The capsulotomy tip 210 is removed 735 from the eye of the patient. The capsulotomy tip 210 may be collapsed to remove the capsulotomy tip 210 through the incision of the eye. In some embodiments, the capsulotomy tip 210 automatically folds and conforms to the incision as it is withdrawn from the eye of the patient.

In some embodiments, the device is designed to perform only some of the steps described above. In one example, the device is a flushing device that generally has the components of the capsulotomy device 120, but does not include a cutting element. The suction cup can be used to attach the device to the lens capsule after a capsulotomy is separately performed to cause the flushing of the capsular bag with fluid. In another embodiment, a modified suction cup is used, such as a cup that has more than one chamber for delivering controlled suction to different areas or for providing a different stress on the capsular bag (prior to cutting the capsule) to affect the epithelial cells. In a further embodiment, a mechanism other than a suction cup is used to attach the flushing device to the opening created via a separate capsulotomy so that flushing can occur. In an additional embodiment, the device includes the cutting element that delivers an electrical pulse, but does not include the suction cup. The electrical pulse delivery is used as the mechanism to reduce or remove the epithelial cells in the capsule. In some cases, a separate flushing device may be used while or after the capsulotomy is performed by the electrical cutting element.

Hydrodissection

Hydrodissection is a process where a liquid is used to loosen and separate the cataract to facilitate its removal. For example, conventional hydrodissection techniques use a small cannula (e.g., a 27-gauge cannula) and a small syringe (e.g., a 3-cc syringe) filled with balanced salt solution (BSS). The syringe is used to dispense BSS to the posterior aspect of the cataract. When a syringe and a cannula are used to perform a hydrodissection, the fluid used to perform the hydrodissection is delivered through a single point and the proper control of the fluid being dispensed may be difficult. In some instances, the doctor performing a hydrodissection may need to move the position of the cannula to direct the fluid being dispensed in different directions to achieve proper hydrodissection. During conventional hydrodissections, as the lens capsule is rotated, LEC may remain under the anterior capsule and at the fornix, which may lead to fibrosis, migration of LEC, and trans-differentiation leading to PCO.

Using the hydrodissection/anti-PCO device, described in detail with reference to FIG. 9A, an automated hydrodissection is performed using a fluid wave that reduces and prevents PCO. During the automated hydrodissection, after a capsulotomy is performed, OVD and/or BSS are pushed through the tip of the device to push the tip of the device off the lens capsule. A 360-degree fluid wave of BSS and/or OVD are injected into the capsular space that begins at the capsulotomy edge and separates LEC from the anterior capsule. This mechanism, combined with complete lens capsular overlap and the rolled edge that is formed during the capsulotomy, mitigate the LEC burden and PCO.

Proper control of the amount of fluid can be achieved through the use of a syringe, peristaltic pump, or roller dispenser coupled with a syringe or pump. Control through a syringe or peristaltic pump requires a response time on the millisecond scale, which may require the use of one or more actuators to control fluid flow (e.g., a voice coil, linear motor, etc.).

In one embodiment, a syringe is snapped into the actuator grips on the front panel of a console, and the piston of the syringe is moved by the actuator. The syringe is filled with an initial volume of air, and the piston is set at an initial position by the actuator such that the pressure in the syringe is at around 1 atm. The fluid line is primed by submerging the suction cup in a beaker of sterile BSS or OVD, and the actuator moves the piston by a predetermined distance. When an optical detector senses the presence of BSS or OVD, the priming stops, while the initial volume air and pressure is maintained within the syringe. The actuator holds the fluid meniscus steady (e.g., within a 1 mm deadband) as the handpiece is pulled out of the beaker and moved around by the user. After the pushrod of the device is extended, the actuator pushes out about 0.05 cc of fluid to eliminate trapped air bubbles in the suction cup. The user has places suction cup in close proximity to the lens capsule, and suction has applied by pulling the piston back to achieve a final pressure of around 0.3 atm (21 inHg). The optical sensors track the BSS/OVD position, and the piston location is known from the actuator position sensor. A force sensor (load cell, strain gauge) may be used to measure the force on the piston as an independent measure of the final pressure (+/− the piston seal friction force). The console may include sensors to measure the barometric pressure and the temperature to make exact calculations of the needed piston movements.

After the capsulotomy is performed, the piston is moved to start fluid release. The trapped air is compressed to eject a desired amount of fluid in a desired amount of time. Because air is compressible, the actuator controlling the piston of the syringe must adjust the pressure as a function of time to keep the velocity of the BSS/OVD constant. The pressure is constant when the pressure reaches 1 atm and the desired amount of liquid has been ejected.

FIG. 9A illustrates a hydrodissection/anti-PCO device, according to one embodiment. The hydrodissection/anti-PCO device 900 includes a hydrodissection/Anti-PCO tip 905 and a handle 950. In some embodiments, the hydrodissection/anti-PCO device further includes a tube 960 for connecting the hydrodissection/anti-PCO device to a pump or a console. The devices referred to in this section are described as anti-PCO devices, but may also be a hydrodissection devices that are not necessarily specifically designed to prevent or reduce PCO.

Figure 9E:
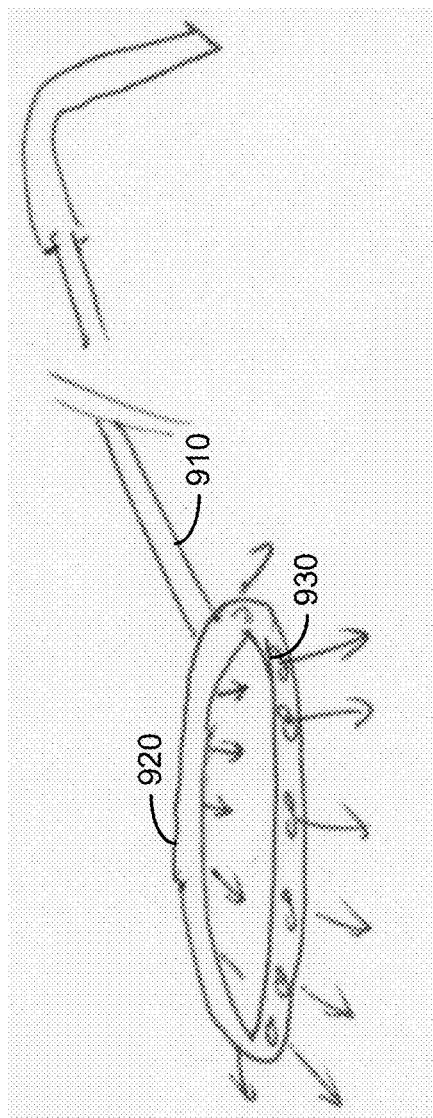
FIG. 9E is a perspective view of the hydrodissection/anti-PCO tip, according to one embodiment.

FIG. 9B-D illustrates a hydrodissection/anti-PCO tip used for hydrodissection/anti-PCO during a capsulotomy procedure, according to one embodiment. FIG. 9B is a top view of the hydrodissection/anti-PCO tip, according to one embodiment. FIG. 9C is a front view of the hydrodissection/anti-PCO tip, according to one embodiment. FIG. 9D is a side view of the hydrodissection/anti-PCO tip, according to one embodiment. FIG. 9E is a perspective view of the hydrodissection/anti-PCO tip, according to one embodiment. The hydrodissection/anti-PCO tip 905 includes a stem 910 and a circular end 920 with multiple holes 930. The circular end 920 is inserted into the subcapsular space for performing a hydrodissection and/or providing anti-PCO effects during a capsulotomy procedure. Since the hydrodissection can be provided with the same instrument as is providing the capsulotomy, the procedure is simplified and fewer instruments are introduced into the eye. In some embodiments, the hydrodissection/anti-PCO tip 905 may also be used for preventing the occurrence of PCO after a capsulotomy procedure has been performed.

The circular end 920 has multiple holes 930 for fluid egress. The fluid is provided to the circular end 920 through a lumen of the stem 910. The holes are disposed around the circumference of the circular end 920 to provide a fluidic wave in a 360° fashion. In some embodiments, the size, number, pattern, shape, and spacing of the holes 930 is adjusted depending on the desired characteristics of the fluidic wave.

The stem 910 is connected to a fluid source delivered by a displacement system such as a roller dispenser, a piston system, or various other pumping mechanisms. For example, the stem 910 may be connected to the console 110. In some embodiments, the fluid being provided to the capsulotomy tip via the stem 910 is balanced salt solution (BSS), viscoelastic gel (visco), sterile water, a hypo-osmotic fluid that will lyse cells, a substance that causes toxicity in lens epithelial cells, or a combination thereof.

Figure 10B:
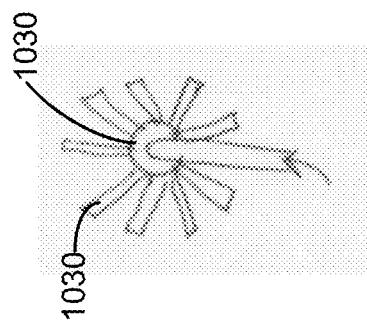
FIG. 10B is a top view of the hydrodissection/anti-PCO tip, according to the second embodiment.
Figure 10C:
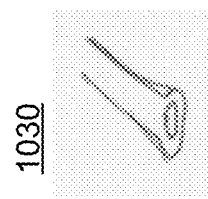
FIG. 10C is a zoomed in view of a fluid dispensing arm of the hydrodissection/anti-PCO tip, according to the second embodiment.
Figure 10A:
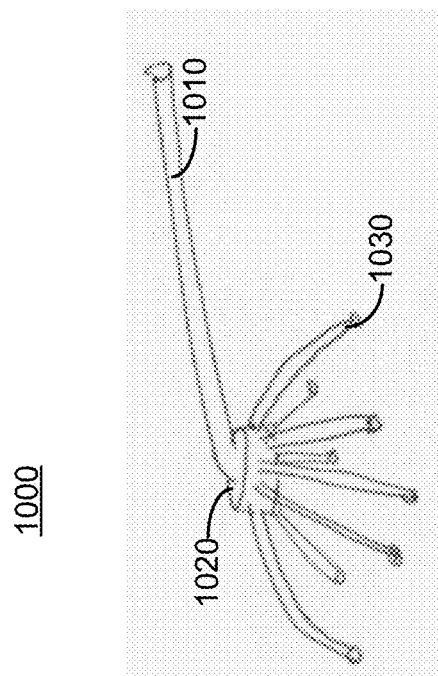
FIG. 10A is a perspective view of the hydrodissection/anti-PCO tip, according to a second embodiment.

FIG. 10A-C illustrate a hydrodissection/anti-PCO tip used for hydrodissection/anti-PCO during a capsulotomy procedure, according to a second embodiment. FIG. 10A is a perspective view of the hydrodissection/anti-PCO tip, according to the second embodiment. FIG. 10B is a top view of the hydrodissection/anti-PCO tip, according to the second embodiment. FIG. 10C is a zoomed in view of a fluid dispensing arm of the hydrodissection/anti-PCO tip, according to the second embodiment.

The hydrodissection/anti-PCO tip 1000 includes a stem 1010 and a circular end 1020 with multiple fluid dispensing arms 1030. The circular end 1020 is inserted into the subcapsular space for performing a hydrodissection and provide anti-PCO effects during a capsulotomy procedure. In one embodiment, the fluid dispensing arms have a tip that is shaped to provide a broad fluid wave and not a narrow stream. The fluid dispensing arms are disposed around the circumference of the circular end 1020 to provide a fluidic wave in a 360° fashion. In some embodiments, the size, number, pattern, shape, and spacing of the fluid dispensing arms 1030 is adjusted depending on the desired characteristics of the fluidic wave.

The stem 1010 is connected to a fluid source delivered by a displacement system such as a roller dispenser, a piston system, or various other pumping mechanisms. For example, the stem 1010 may be connected to the console 110. In some embodiments, the fluid being provided to the hydrodissection/anti-PCO tip via the stem 1010 is balanced salt solution (BSS), viscoelastic gel (visco), sterile water, a hypo-osmotic fluid that will lyse cells, a substance that causes toxicity in lens epithelial cells, or a combination thereof.

In some embodiments, the hydrodissection/anti-PCO tip is part of a hydrodissection/anti-PCO device for performing a hydrodissection and provide anti-PCO effects during a capsulotomy procedure. In other embodiments, the hydrodissection/anti-PCO tip is part of a capsulotomy device. For example, the hydrodissection tip may be combined with the capsulotomy tip 210 of the capsulotomy device 120 of FIG. 2A.

In some embodiments, the hydrodissection/anti-PCO tip has other designs. For example, the hydrodissection/anti-PCO tip may have a circular end coupled to multiple fluid dispensing arms. FIG. 11A-C illustrates a hydrodissection/anti-PCO tip used for hydrodissection/anti-PCO during a capsulotomy procedure, according to a third embodiment. FIG. 11A is a top view of the hydrodissection/anti-PCO tip, according to the third embodiment. FIG. 11B is a front view of the hydrodissection/anti-PCO tip, according to the third embodiment. FIG. 11C is a side view of the hydrodissection/anti-PCO tip, according to the third embodiment. The hydrodissection/anti-PCO tip 1105 includes a circular end 1120 attached to a stem 1110. The circular end 1120 has multiple fluid dispensing arms 1130. The circular end 1120 and the fluid dispensing arms 1130 are inserted into the subcapsular space for performing a hydrodissection and providing anti-PCO effects during a capsulotomy procedure.

Each of the hydrodissection/anti-PCO devices described throughout may be used as part of a capsulotomy device or separate from the capsulotomy device as an independent instrument. The fluid is delivered with each of these generally more evenly than conventional hydrodissection fluid delivery techniques as the fluid is delivered in a 360° manner around all sides of the lens as opposed to being delivered on one side around the lens and returning on the other side of the lens.

Figure 12:
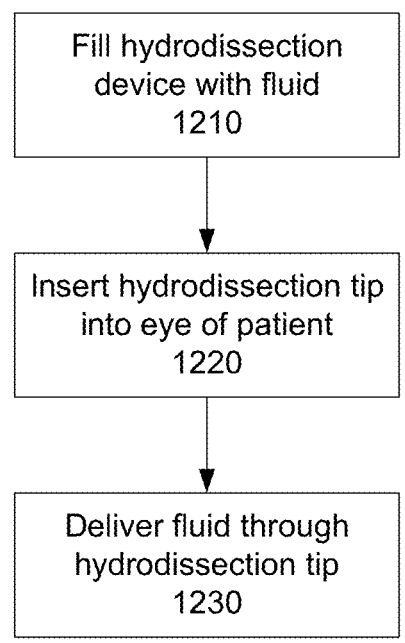
FIG. 12 illustrates a flow diagram for the operation of the hydrodissection/anti-PCO device, according to one embodiment.

FIG. 12 illustrates a flow diagram for the operation of the hydrodissection/anti-PCO device, according to one embodiment. The hydrodissection/anti-PCO device is filled with fluid (e.g., balanced salt solution (BSS), viscoelastic gel (visco), sterile water, or a combination thereof). In some embodiments, the fluid enters the device through the hydrodissection/anti-PCO tip 905. In particular, the fluid can be added through the holes 930 of the hydrodissection tip 905. In some embodiments, the hydrodissection/anti-PCO device is filled with fluid by placing the hydrodissection tip 905 inside a beaker with the fluid, attaching a syringe to the end of the hydrodissection/anti-PCO device, and drawing the plunger of the syringe. In some embodiments, the roller dispenser 130 is attached to the hydrodissection device prior to filling the hydrodissection/anti-PCO device with fluid. In some embodiments, the hydrodissection/anti-PCO device is filled with fluid via a fluid reservoir that is attached to the device. The reservoir may remain attached to the device during surgery or may be removed.

In some embodiments the hydrodissection/anti-PCO device is filled 1210 with fluid prior to connecting the hydrodissection/anti-PCO device to the console 110. In another embodiment, a peristaltic pump is built into the console, and it automatically primes the line after it is placed in the console. Once the hydrodissection/anti-PCO device is filled with the fluid, the hydrodissection/anti-PCO device can be connected to the console via a fluid isolator. In other embodiments, the hydrodissection/anti-PCO device is connected to the console 110, and the console 110 performs the steps to fill the hydrodissection/anti-PCO device with fluid.

The hydrodissection/anti-PCO tip 905 is inserted 1220 into the eye of a patient. In some embodiments, the hydrodissection/anti-PCO tip 905 is inserted into the subcapsular space of the eye of the patient. The hydrodissection/anti-PCO tip 905 is inserted into the eye of the patient through a corneal incision by collapsing the hydrodissection/anti-PCO tip 905 to reduce the width of the capsulotomy tip 905 prior to inserting the hydrodissection/anti-PCO tip into the eye of the patient. After the hydrodissection/anti-PCO tip 905 has been inserted into the eye of the patient, the collapsed hydrodissection/anti-PCO tip 905 is expanded until the hydrodissection/anti-PCO tip 905 generally regains the shape it had prior to collapsing.

Fluid is delivered 1230 or advanced through the hydrodissection/anti-PCO tip 905. In some embodiments, the fluid delivered is a balanced salt solution (BSS), viscoelastic gel (visco), sterile water, a hypo-osmotic fluid that will lyse cells, a substance that causes toxicity in lens epithelial cells, or a combination thereof. The fluid is delivered through the holes 930 or fluid dispensing arms 1030 of the hydrodissection/anti-PCO tip 905.

Intraocular Lens

An in intraocular lens (IOL) is a lens implanted in the eye via a capsulotomy formed using the capsulotomy device. The IOL designed for use with or packaged with the capsulotomy device is different from conventional IOLs due to the ability of the capsulotomy device to provide an improved capsulotomy that reduces or eliminates PCO. Conventional IOLs have evolved over time to have a square edge that increases the risk of positive or negative dysphotopsia, and some have net smaller optic diameters to allow relatively dramatic edge configurations to minimize the risk of PCO. The claimed capsulotomy device can prevent this increase in positive or negative dysphotopsia by allowing the edge configuration of IOLs used with the device to be less square-edged (e.g., without any edges that are square, such that it is more circular in shape, with rounded edges or with less dramatic edges or edges that are less straight) than conventional IOLs) or non-square edged. These IOLs can be specially designed for use with the capsulotomy device. They can be, for example, form a perfect circle or be generally circular, can be oval, or can be other shapes that do not have sharp edges or form right angles at their edges, or shapes that only have curved sides without any straight edges. In these embodiments, the device comprises a capsulotomy and IOL system packaged into a single item for purchase by a licensed ophthalmic practitioner or authorized entity. The capsulotomy device is designed as one of the devices described throughout this description and it is packaged with an IOL designed for use with the capsulotomy device, where the IOL is modified from conventional IOLs in the manner described above (e.g., less square- or straight-edged, possibly more round-edged or circular in shape).

Figure 13:
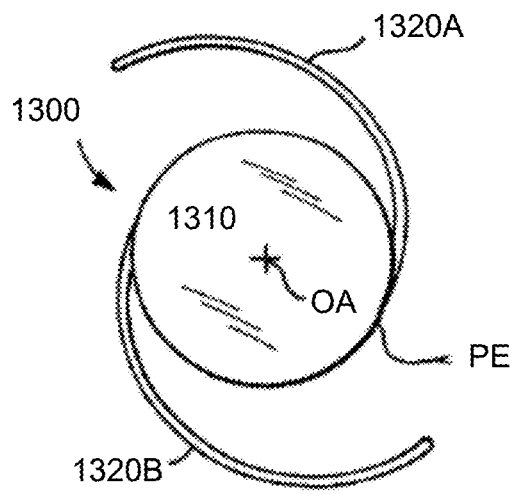
FIG. 13 illustrates a top view of a conventional intraocular lens (IOL).
Figure 14:
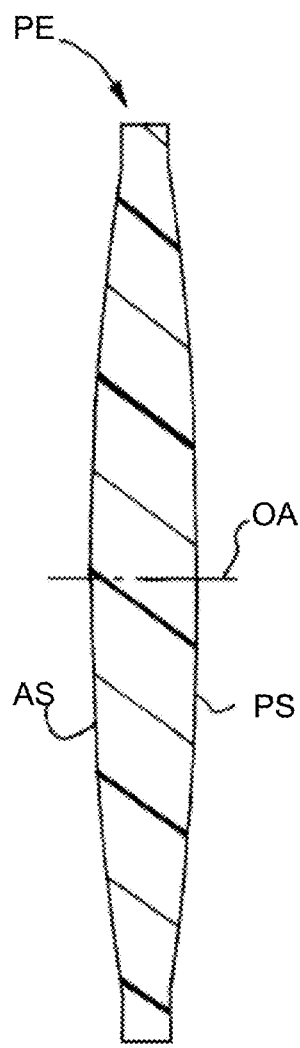
FIG. 14 illustrates a cross sectional view of a conventional IOL.

FIG. 13 illustrates a top view of a conventional intraocular lens (IOL). FIG. 14 illustrates a cross sectional view of a conventional IOL. The IOL 1300 includes an optic 1310 and multiple fixation members 1320. For example, in the IOL of FIG. 13, the IOL includes two fixation members 1320A and 1320B. The optic 1310 focuses light on or near the retina of the eye. The optical axis OA passes through the center of optic 1310 in a direction transverse to the plane of the optic 1310. Furthermore, the IOL has a convex anterior surface AS, a convex posterior surface PS, and a peripheral edge PE. The peripheral edge PE has angled corners, which is conventionally believed to provide inhibition of cell growth onto the optic 1310, and thus, preventing the development of PCO. However, as described above, the angled corners of the optic 1310 can create adverse optical effects such as positive and negative dysphotopsias. Thus an improved IOL that reduces the occurrence of the adverse optical effects associated with IOLs having angled corners, while maintaining a level of PCO prevention is desired.

Since the capsulotomy device described herein can reduce the development of PCO, an IOL that does not have angled edges may be used without increasing the likelihood of PCO occurring compared to the case where a conventional capsulotomy device is used in conjunction with a conventional IOL. As such, the negative effects of using an IOL with angled edges can be reduced.

Figure 15C:
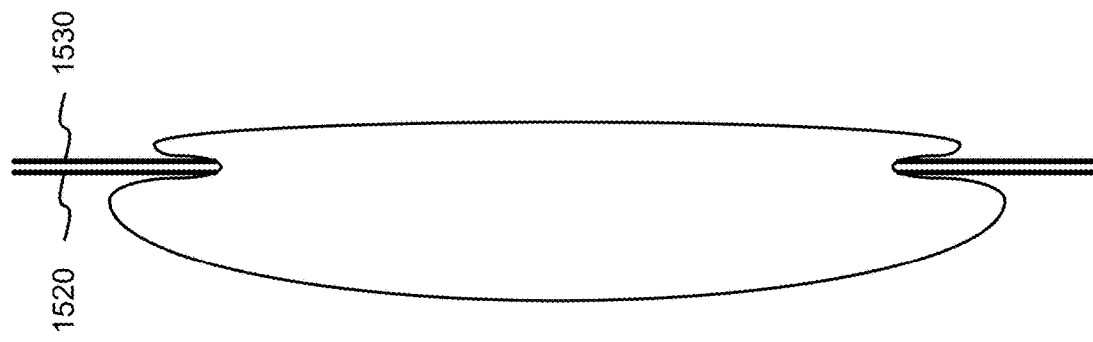
FIG. 15C illustrates the IOL design from FIG. 15A in the capsular bag with anterior and posterior capsular flap retention, according to one embodiment.
Figure 15B:
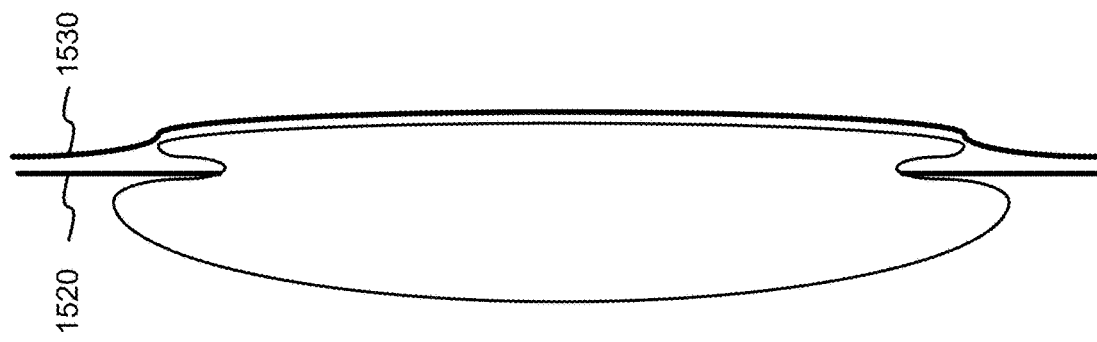
FIG. 15B illustrates the IOL design from FIG. 15A in the capsular bag with anterior capsular flap retention, according to one embodiment.
Figure 15A:
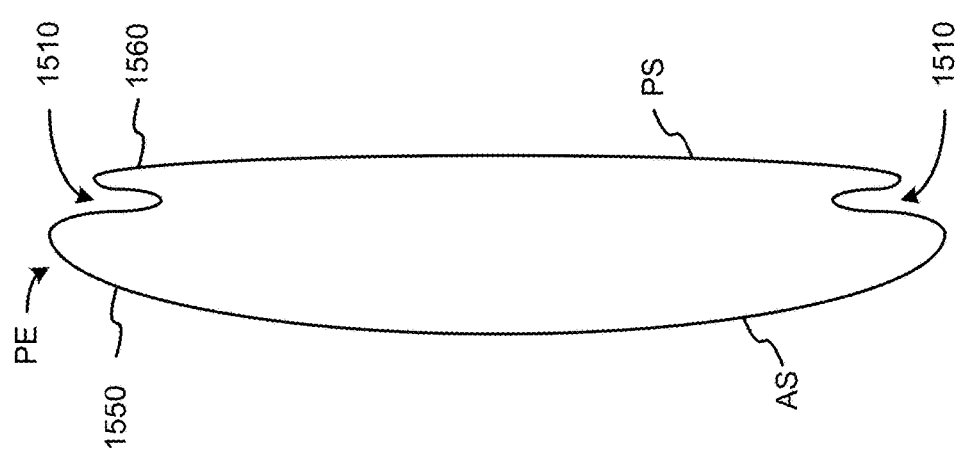
FIG. 15A illustrates an intraocular lens (IOL) design with a radially oriented channel located on the located on the posterior side of the IOL adjacent to the outer diameter, according to one embodiment.

FIG. 15A illustrates an intraocular lens (IOL) design with a radially oriented channel located on the posterior side of the IOL adjacent to the outer diameter, according to one embodiment. FIG. 15B illustrates the IOL design from FIG. 15A in the capsular bag with anterior capsular flap retention, according to one embodiment. FIG. 15C illustrates the IOL design from FIG. 15A in the capsular bag with anterior and posterior capsular flap retention, according to one embodiment.

The IOL design of FIG. 15A includes a peripheral edge PE that is rounded along its surface. In some embodiments, the peripheral edge PE of the IOL has rounded edges or sides. Moreover, the peripheral edge PE includes flap channel 1510. The flap channel 1510 are configured to be attached to an anterior capsule flap (as shown in FIG. 15B), or attached to both an anterior capsule flap and a posterior capsule flap (as shown in FIG. 15C) that is formed during capsulotomy.

The peripheral edge PE includes an anterior edge 1550 and a posterior edge 1560. In the Embodiment of FIG. 15A, the anterior edge 1550 is larger than the posterior edge 1560. Thus, the flap channel 1510 are shifted closer to the posterior side of the IOL.

In some embodiments, the IOL includes a single flap channel that is continuous around the edge of the IOL. That is, the flap channel is a ring that located in the peripheral edge PE of the IOL.

Figure 16C:
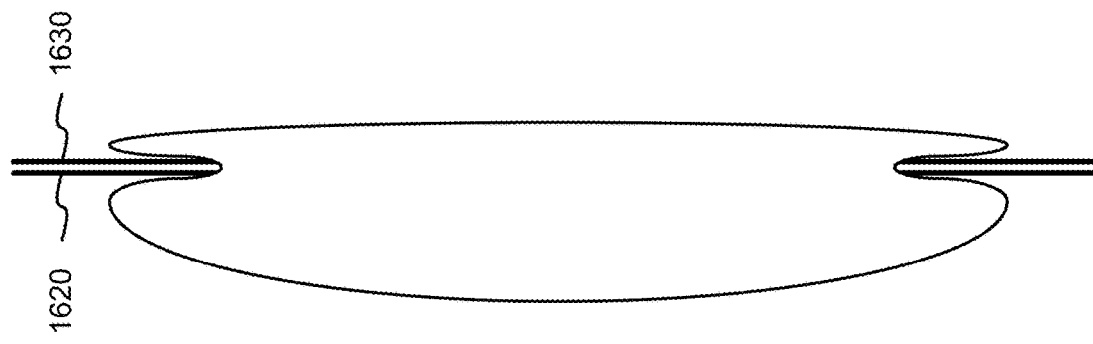
FIG. 16C illustrates the IOL design from FIG. 16A in the capsular bag with anterior and posterior capsular flap retention, according to one embodiment.
Figure 16B:
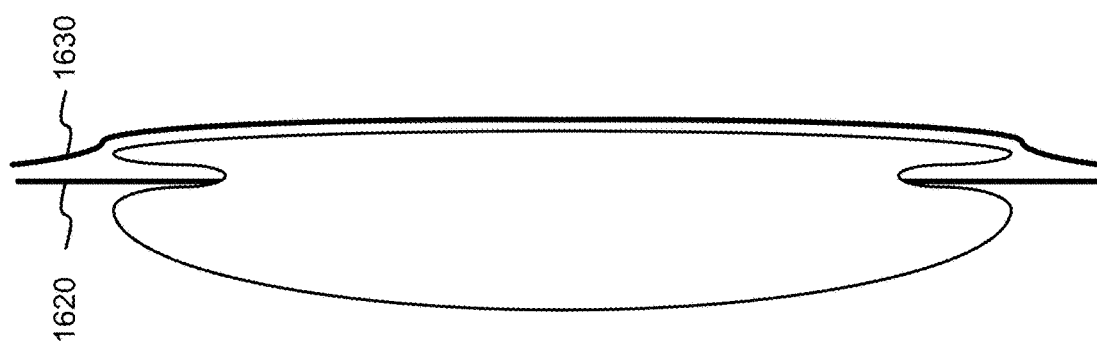
FIG. 16B illustrates the IOL design from FIG. 16A in the capsular bag with anterior capsular flap retention, according to one embodiment.
Figure 16A:
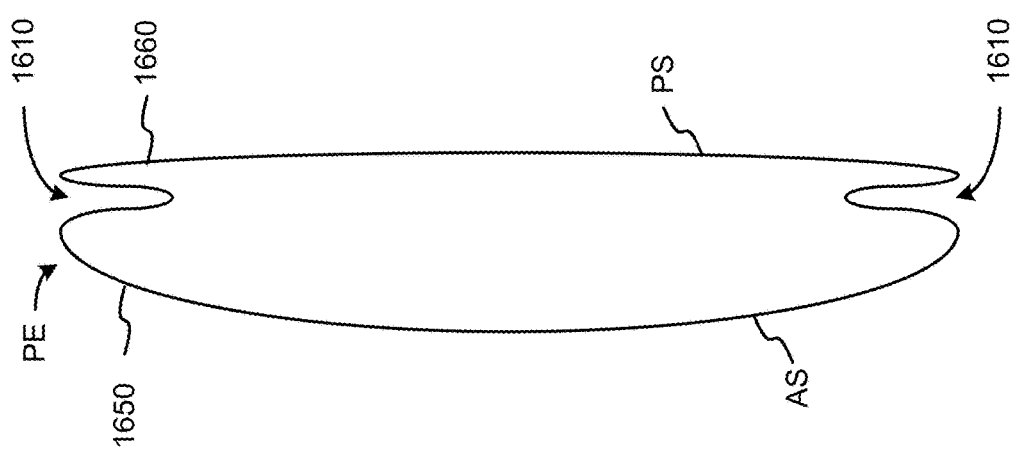
FIG. 16A illustrates an IOL design, with a radially oriented channel located on the IOL's diametrical surface, according to one embodiment.

FIG. 16A illustrates an IOL design, with a radially oriented channel located on the IOL's diametrical surface, according to one embodiment. FIG. 16B illustrates the IOL design from FIG. 16A in the capsular bag with anterior capsular flap retention, according to one embodiment. FIG. 16C illustrates the IOL design from FIG. 16A in the capsular bag with anterior and posterior capsular flap retention, according to one embodiment.

Similar to the IOL design of FIG. 15A, the IOL design of FIG. 16A includes a peripheral edge PE that is rounded along its surface. Moreover, the peripheral edge PE includes flap channel 1610. The flap channel 1610 are configured to be attached to an anterior capsule flap (as shown in FIG. 16B), or attached to both an anterior capsule flap and a posterior capsule flap (as shown in FIG. 16C) that is formed during capsulotomy.

The peripheral edge PE includes an anterior edge 1650 and a posterior edge 1660. In the Embodiment of FIG. 16A, the anterior edge 1650 and the posterior edge 1660 have substantially equal size. Thus, the flap channel 1610 are at or near the center of the IOL.

Figure 17C:
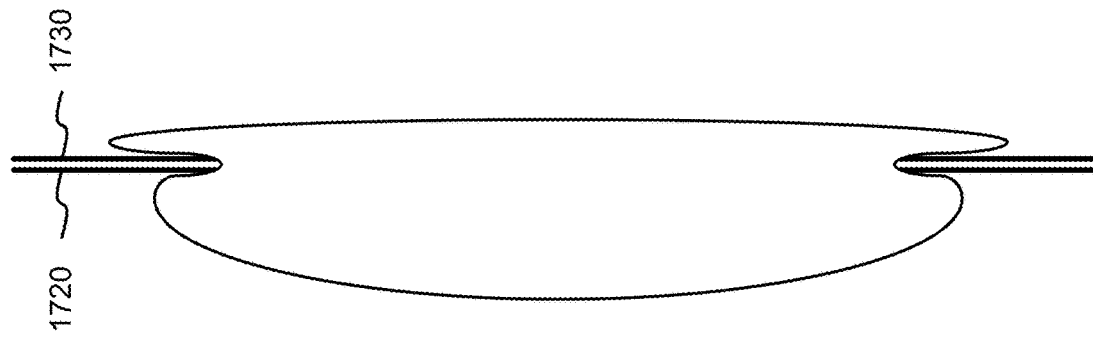
FIG. 17C illustrates the IOL design from FIG. 17A in the capsular bag with anterior and posterior capsular flap retention, according to one embodiment.
Figure 17B:
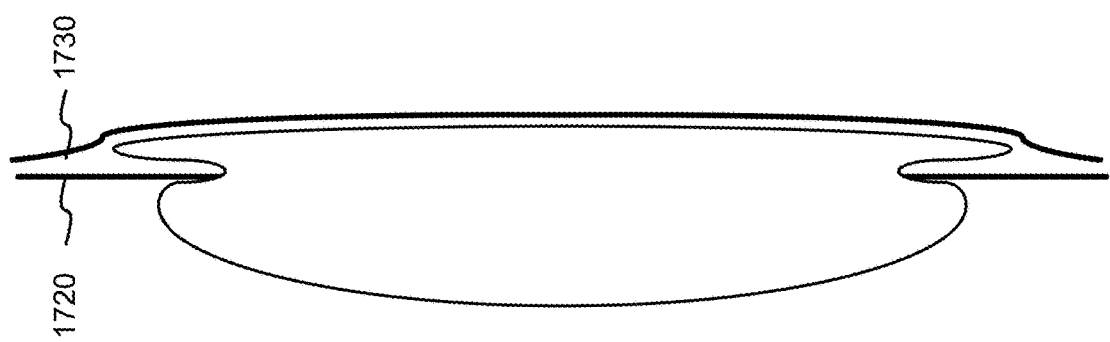
FIG. 17B illustrates the IOL design from FIG. 17A in the capsular bag with anterior capsular flap retention, according to one embodiment.
Figure 17A:
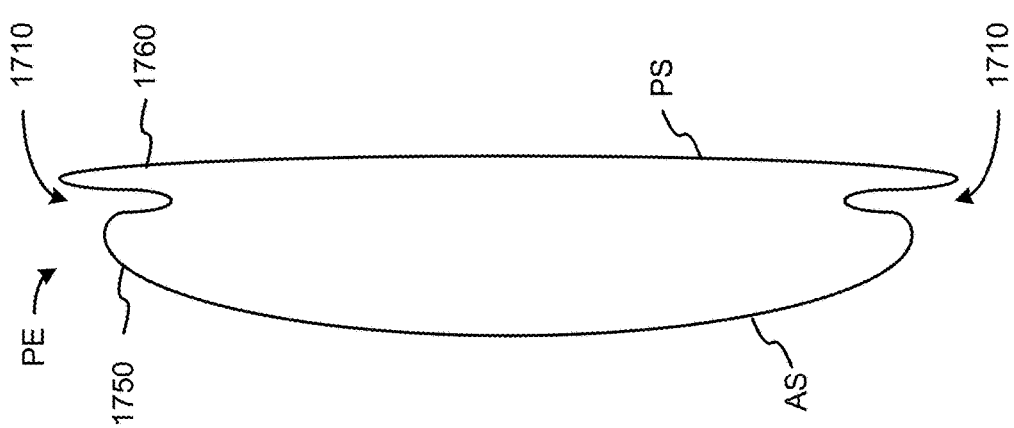
FIG. 17A illustrates an IOL design with a radially oriented channel located on the anterior side of the IOL adjacent to the outer diameter, according to one embodiment.

FIG. 17A illustrates an IOL design with a radially oriented channel located on the anterior side of the IOL adjacent to the outer diameter, according to one embodiment. FIG. 17B illustrates the IOL design from FIG. 17A in the capsular bag with anterior capsular flap retention, according to one embodiment. FIG. 17C illustrates the IOL design from FIG. 17A in the capsular bag with anterior and posterior capsular flap retention, according to one embodiment.

Similar to the IOL design of FIG. 15A, the IOL design of FIG. 17A includes a peripheral edge PE that is rounded along its surface. Moreover, the peripheral edge PE includes flap channel 1710. The flap channel 1710 are configured to be attached to an anterior capsule flap (as shown in FIG. 17B), or attached to both an anterior capsule flap and a posterior capsule flap (as shown in FIG. 17C) that is formed during capsulotomy.

The peripheral edge PE includes an anterior edge 1750 and a posterior edge 1760. In the Embodiment of FIG. 17A, the posterior edge 1760 is larger than the anterior edge 1750. Thus, the flap channel 1710 are shifted closer to the anterior side of the IOL.

Figure 18B:
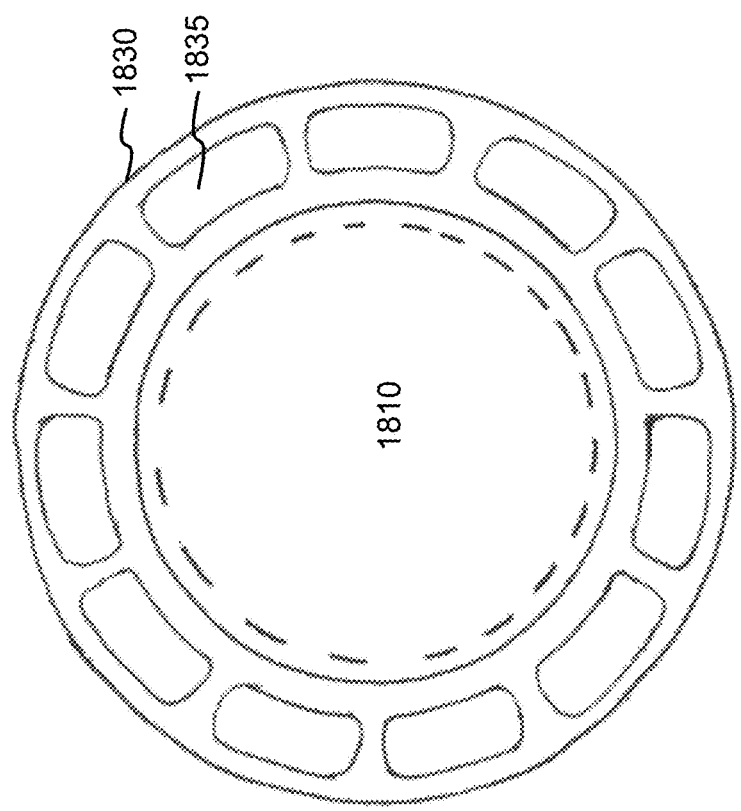
FIG. 18B illustrates a top view of the IOL design from FIG. 17A with a continuous retainer consisting of multiple openings, according to one embodiment.
Figure 18A:
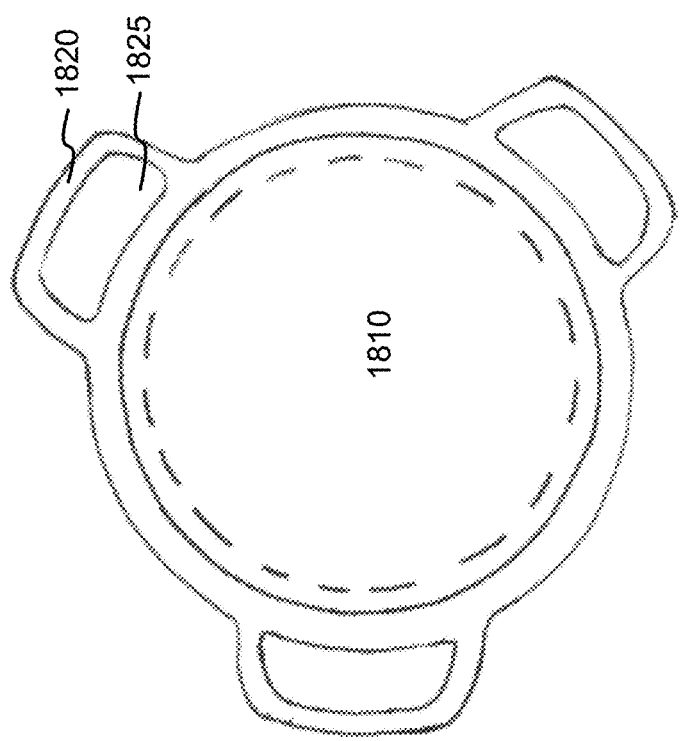
FIG. 18A illustrates a top view of the IOL design from FIG. 17A with 3 retainers each with its own opening, according to one embodiment.

FIG. 18A illustrates a top view of the IOL design from FIG. 17A with 3 retainers, according to one embodiment. The retainers aid in the long term stability of the IOL in case of capsule rupture. The IOL design of FIG. 18A includes three retainers 1820 that are placed between the anterior and posterior capsule surfaces during surgery. Once the anterior and posterior capsule fuse in the opening area, the retainer provides for improved long term IOL stability. Each of the retainers 1820 includes an opening 1825. In some embodiments, the retainers 1820 have a thickness of about 0.2 mm and a width of about 0.4 mm. Moreover, the openings 1825 may have a length of about 1.5 mm and a width of about 2.5 mm. In one embodiment, the retainers 1820 extend radially from the optic 1810 and are symmetrically arranged with respect to the central axis of the optic 1810. In one embodiment, the optic 1810 has a diameter of about 7 mm and the IOL has a total diameter (including the retainers 1820) of about 11 mm.

FIG. 18B illustrates a top view of the IOL design from FIG. 17A with a continuous retainer consisting of multiple openings, according to one embodiment. The continuous retainer structure, with openings, would be expected to provide more stability than a design with only 3 retainers. The IOL design of FIG. 18B includes a retainer structure 1830 with multiple openings 1835. In some embodiments, the retainer structure 1830 radially extends about 2 mm from the optic edge 1810. Moreover, the openings 1835 have a length of about 1.5 mm and a width of about 2.5 mm. In one embodiment, the optic 1810 has a diameter of about 7 mm and the IOL has a total diameter (including the retainer structure 1830) of about 11 mm.

Figure 19:
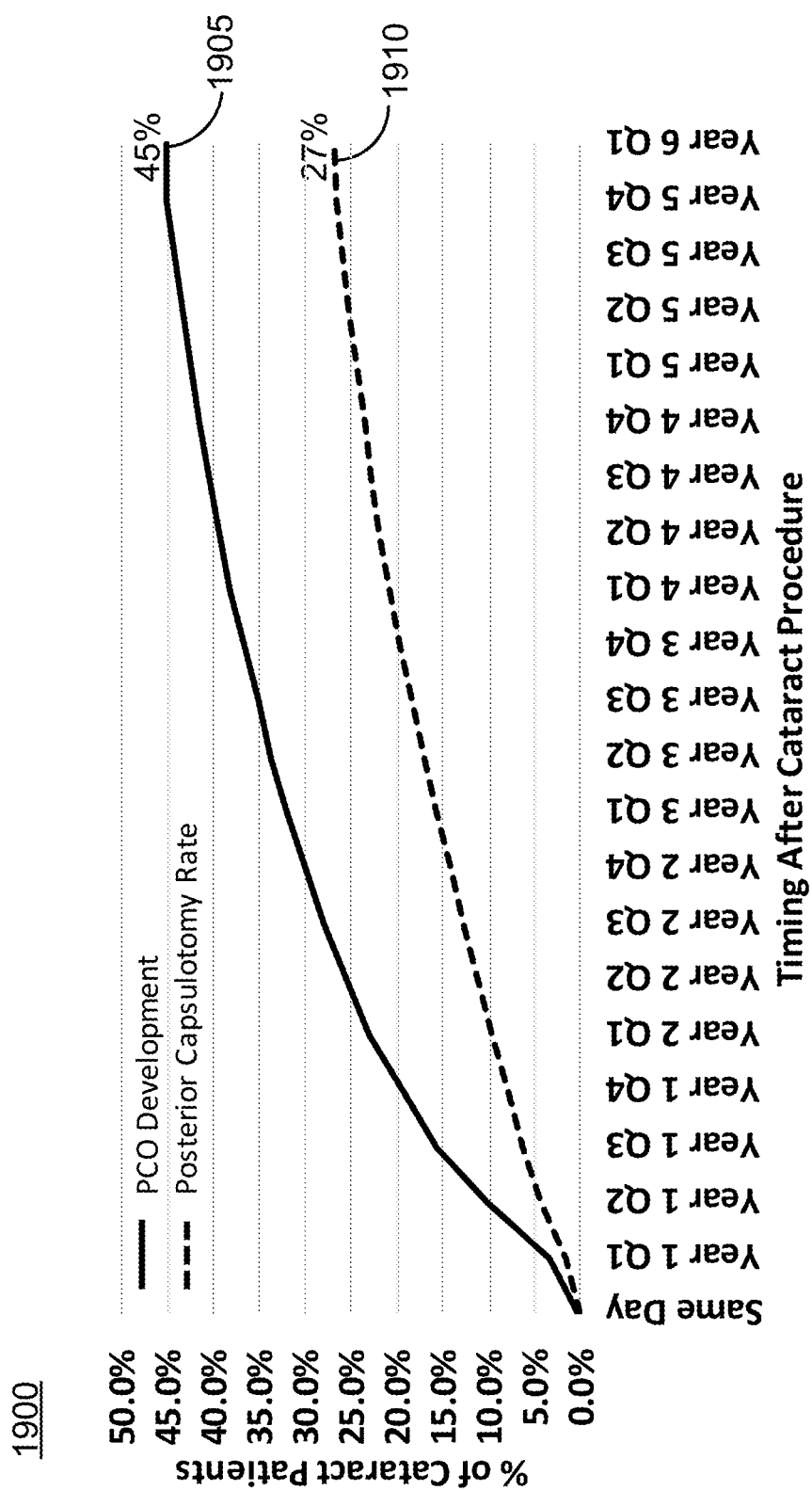
FIG. 19 illustrates data representative of the occurrence of PCO in cataract patients that have had capsulotomies performed.

FIG. 19 illustrates data representative of the occurrence of PCO in cataract patients that have had capsulotomies performed. The graph 1900 shows the percentage of cataract patients who develop PCO 1905. In a study of cataract surgeries completed in 2011, it was observed that the prevalence of PCO in cataract patients after surgery increases over time. In particular, 45% of patients received a diagnosis of PCO within six years of cataract surgeries completed in 2011.

The graph 1900 also illustrates the percentage 1910 of cataract patients who undergo PCO corrective surgeries, known as posterior capsulotomies. Like the rate of PCO development in patients, posterior capsulotomies are increasingly performed over time. In the same study, it was observed that up to 27% of cataract patients underwent posterior capsulotomies within six years of cataract surgery. While posterior capsulotomies are effective in reducing and/or removing PCO, additional risks and complications can occur with any surgery. Therefore, there is an unmet medical need to perform capsulotomies in a way that reduces PCO development post-surgery and mitigates the need for posterior capsulotomies.

FIG. 20 illustrates the percentage of cataract patients who develop PCO when capsulotomies are performed using various capsulotomy techniques. In a retrospective, case control study, patients (N=60) underwent a capsulotomy performed using either a Zepto device (a capsulotomy device of the present invention) or a manual technique (not involving a capsulotomy device of the present invention). The first group of patients (N=37, the "Zepto" group) underwent capsulotomies in which a Zepto capsulotomy device was used to produce a strong, curled capsulorhexis edge, as described in FIG. 8A. The second group of patients 23, the "CCC" group) underwent capsulotomies in which a manual, continuous-tear curvilinear capsulorhexis ("CCC", or the "CCC method") was used to produce a circular edge, as described in FIG. 8C. Within 21 months of the capsulotomy creation, 77% of patients in the CCC group developed PCO, while only 20% of patients in the Zepto group developed PCO in the same timeframe. The ability of the Zepto capsulotomy device to reduce PCO development in patients relative to the CCC method was found to be statistically significant (p<0.0001). It was concluded that there is a significant correlation between PCO development and the type of device used and edge formed during a capsulotomy.

An adjusted data set was produced from the unadjusted data set by removing seven abnormal cases. In particular, five cases from the Zepto group were removed because the patients underwent irregular capsulotomies, and two cases in the CCC group were removed because the patients developed phimosis. Results from the adjusted data set are consistent with the results from the unadjusted dataset. In particular, there were significantly fewer patients with PCO in the Zepto group (8%) than in the CCC group (83%) (p<0.0001). It can be concluded that the Zepto capsulotomy device is more effective in reducing PCO in cataract surgery patients than the CCC method.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed:

1. A surgical device comprising:
   a suction cup including an inner diameter wall, an outer diameter wall, and a roof, the inner diameter wall, the outer diameter wall, and the roof forming a channel;
   a stem coupled to the suction cup, the stem including a lumen that is in fluid communication with the suction cup, the lumen configured to be coupled to the channel;
   a lip coupled to the outer diameter wall, the lip configured to be pulled against a capsular membrane of an eye to form a low leakage seal to allow a pressure inside the channel to decrease;
   an electrical cutting element for cutting tissue, wherein the electrical cutting element is mounted on an underside of the suction cup, the electrical cutting element configured to cause a shrinkage of collagen fibers resulting in an upward fold of the cut tissue; and
   a dispenser coupled to the lumen of the stem, the dispenser configured to dispense a predetermined amount of fluid through the lumen to the suction cup.

2. The surgical device of claim 1, wherein the electrical cutting element includes an electrical lead, the electrical lead configured to send an electrical pulse to the electrical cutting element.

3. The surgical device of claim 1, wherein the suction cup is circular in shape, and wherein the channel formed by the inner wall, the outer wall, and the roof has a ring shape.

4. The surgical device of claim 1, wherein the suction cup comprises:
   a baffle disposed near the stem, the baffle for equalizing a flow rate around the suction cup.

5. The surgical device of claim 1, wherein the dispenser comprises:
   a housing including a bottom surface and a side surface, a track disposed on the side surface of the housing;
   a roller configured to move along the track of the housing;
   a compliant surface disposed on the bottom surface of the housing; and
   a tube disposed between the roller and the compliant surface, the tube of the roller dispenser in fluid communication with the lumen of the stem, wherein the tube is configured to allow fluid to flow through the roller dispenser when the roller is at a first end of the track, wherein the roller is configured to clamp the tube as the roller is advanced along the track, and wherein after the tube is clamped by the roller, the roller is configured to push a fluid disposed inside the tube as the roller is further advanced along the track towards a second end of the track.

6. The surgical device of claim 5, wherein the compliant surface is composed of a foam material to allow the roller to be advanced along the track up to the second end of the track after the roller has clamped the tube.

7. The surgical device of claim 5, wherein the compliant surface is composed of a soft material that allows the compliant surface to be compressed by a force exerted when the roller is clamping the tube.

8. The surgical device of claim 1, wherein the dispenser is configured to dispense a volume of fluid between 0.02 milliliters and 1.0 milliliter.

9. The surgical device of claim 1, wherein the fluid hydrodissects a capsule away from a lens of an eye of a patient.

10. The surgical device of claim 1, wherein the dispenser comprises:
    a housing including a bottom surface, a side surface, and a track disposed on the side surface of the housing;
    a roller configured to move along the track of the housing;
    a tube disposed between the roller and the bottom surface, the tube in fluid communication with the lumen of the stem, wherein the tube is configured to allow fluid to flow through the dispenser when the roller is at a first end of the track, wherein the roller is configured to pinch the tube shut as the roller is advanced along the track, and wherein after the tube is clamped by the roller, the roller is configured to push a fluid disposed inside the tube as the roller is further advanced along the track towards a second end of the track; and
    wherein the track comprises a first portion to guide the roller for pinching the tube closed, and a second portion that runs parallel to the bottom surface of the housing.

11. A package comprising the surgical device of claim 1 and an intraocular lens having only rounded edges.

12. A surgical device comprising:
    a suction cup including an inner diameter wall, an outer diameter wall, and a roof, an inner membrane coupled to the inner diameter wall, and a plurality of standoffs on the inner membrane;
    a stem coupled to the suction cup, the stem including a lumen that is in fluid communication with the suction cup;
    an electrical cutting element for cutting tissue, wherein the electrical cutting element is mounted on an underside of the suction cup, the electrical cutting element configured to cause a shrinkage of collagen fibers resulting in an upward fold of the cut tissue; and
    a dispenser coupled to the lumen of the stem, the dispenser configured to dispense a predetermined amount of fluid through the lumen to the suction cup.

13. The surgical device of claim 12, wherein the electrical cutting element includes an electrical lead, the electrical lead configured to send an electrical pulse to the electrical cutting element.

14. The surgical device of claim 12, wherein the suction cup is circular in shape, and wherein the channel formed by the inner wall, the outer wall, and the roof has a ring shape.

15. The surgical device of claim 12, wherein the suction cup comprises:
    a baffle disposed near the stem, the baffle for equalizing a flow rate around the suction cup.

16. The surgical device of claim 12, wherein the dispenser comprises:
    a housing including a bottom surface and a side surface, a track disposed on the side surface of the housing;
    a roller configured to move along the track of the housing;
    a compliant surface disposed on the bottom surface of the housing; and
    a tube disposed between the roller and the compliant surface, the tube of the roller dispenser in fluid communication with the lumen of the stem, wherein the tube is configured to allow fluid to flow through the roller dispenser when the roller is at a first end of the track, wherein the roller is configured to clamp the tube as the roller is advanced along the track, and wherein after the tube is clamped by the roller, the roller is configured to push a fluid disposed inside the tube as the roller is further advanced along the track towards a second end of the track.

17. The surgical device of claim 16, wherein the compliant surface is composed of a foam material to allow the roller to be advanced along the track up to the second end of the track after the roller has clamped the tube.

18. The surgical device of claim 16, wherein the compliant surface is composed of a soft material that allows the compliant surface to be compressed by a force exerted when the roller is clamping the tube.

19. The surgical device of claim 12, wherein the dispenser is configured to dispense a volume of fluid between 0.02 milliliters and 1.0 milliliter.

20. The surgical device of claim 12, wherein the fluid hydrodissects a capsule away from a lens of an eye of a patient.

21. The surgical device of claim 12, wherein the dispenser comprises:
    a housing including a bottom surface, a side surface, and a track disposed on the side surface of the housing;
    a roller configured to move along the track of the housing;
    a tube disposed between the roller and the bottom surface, the tube in fluid communication with the lumen of the stem, wherein the tube is configured to allow fluid to flow through the dispenser when the roller is at a first end of the track, wherein the roller is configured to pinch the tube shut as the roller is advanced along the track, and wherein after the tube is clamped by the roller, the roller is configured to push a fluid disposed inside the tube as the roller is further advanced along the track towards a second end of the track; and
    wherein the track comprises a first portion to guide the roller for pinching the tube closed, and a second portion that runs parallel to the bottom surface of the housing.

22. A package comprising the surgical device of claim 12 and an intraocular lens having only rounded edges.

* * * * *